US011690923B2

(12) United States Patent
Roodt et al.

(10) Patent No.: US 11,690,923 B2
(45) Date of Patent: Jul. 4, 2023

(54) MULTINUCLEAR COMPLEXES AND THEIR PREPARATION

(71) Applicants: UNIVERSITY OF THE FREE STATE, Bloemfontein (ZA); UNIVERSITÄT ZÜRICH, Zürich (ZA)

(72) Inventors: Andreas Roodt, Bloemfontein (ZA); Roger Ariel Alberto, Winterthur (CH); Angelo Frei, Bischofszell (CH); Petrus Pennie Mokolokolo, Kroonstad (ZA); Robin Kim Bollinger, Wettingen (CH); Alice Brink, Bloemfontein (ZA); Dumisani Vincent Kama, Bultfontein (ZA)

(73) Assignees: UNIVERSITY OF THE FREE STATE, Bloemfontein (ZA); UNIVERSITAT ZURICH, Zurich (ZA)

( * ) Notice: Subject to any disclaimer, the term of this patent is extended or adjusted under 35 U.S.C. 154(b) by 0 days.

(21) Appl. No.: 17/379,011

(22) Filed: Jul. 19, 2021

(65) Prior Publication Data

US 2021/0393813 A1 Dec. 23, 2021

Related U.S. Application Data

(62) Division of application No. 16/957,000, filed as application No. PCT/IB2018/060506 on Dec. 21, 2018, now abandoned.

(30) Foreign Application Priority Data

Dec. 21, 2017 (ZA) .................................. 2017/08729

(51) Int. Cl.
*A61K 51/04* (2006.01)
(52) U.S. Cl.
CPC ................................ *A61K 51/0478* (2013.01)
(58) Field of Classification Search
CPC ..................................................... A61K 51/04
See application file for complete search history.

(56) References Cited

U.S. PATENT DOCUMENTS

2004/0018147 A1* 1/2004 Duatti ................ A61K 51/0476
534/14
2020/0330623 A1  10/2020 Roodt et al.

FOREIGN PATENT DOCUMENTS

| JP | H06-92869 A | 4/1994 |
| JP | 2012-193199 A | 10/2012 |
| KR | 10-2012-0092760 A | 8/2012 |
| WO | 2019/123409 A1 | 6/2019 |

OTHER PUBLICATIONS

Tsutomu Takayama et al. Phenoxo-bridged dimeric structure of technetium(I) tricarbonyl complex with schiff base ligand, Journal of Nuclear and Radiochemical Sciences, 6(3), 149-152. (Year: 2005).*
Ulrich Abram et al. Tricarbonyl complexes of rhenium(I) and technetium(I) with thiourea derivatives, Journal of Organometallic Chemistry, 689, 2066-2072. (Year: 2004).*
Alexandre Boulay et al. First dinuclear Re/Tc complex as a potential bimodal Optical/SPECT molecular imaging agent, Dalton Transactions, 40, 6206-6209. (Year: 2011).*
International Search Report for PCT/IB2018/060506 dated Mar. 21, 2019, all pages.
Basil Kanellakopulos et al., "Darstellung und Rontgenstrukturanalyse des polymeren Trimethylstannylpertechnetats", Zeitschrift Fur Naturforschung B, vol. 46, No. 1, Jan. 1, 1991, pp. 15-18, XP55566948, the whole document.
Boulay et al., "First dinuclear RE/TC complex as a potential bimodal Optical/SPECT molecular imaging agent," *Dalton Trans.*, 2011, 40, 6206-6209, DOI: 10.1039/c0dt01397h, www.rsc.org/dalton.
Bing Ma et al., "Bifunctional HPPH-$N_2S_2$ $^{99m}$Tc conjugates as tumor imaging agents: synthesis and biodistribution studies," *Journal of Porphyrins and Phthalocyanines* 2003; 7: 500-507, 8 pages.
Braband et al., "Tricarbonyl complexes of rhenium(I) and technetium(I) with thiourea derivatives," *Journal of Organometallic Chemistry* 689 (2004) 2066-2072 www.elsevier.com/locate/jorganchem.
Elisabeth Oehlke et al., "Synthesis, Characterization, and Structures of R 3 EOTc0 3 Complexes (E=C, Si, Ge, Sn, Pb) and Related Compounds", Inorganic Chemistry, vol. 49, No. 7, Apr. 5, 2010, pp. 3525-3530, XP55566967, Easton, US ISSN: 0020-1669, DOI: 10.1021/ic1001094, the whole document.
Francois et al., "A functionalized heterobimetallic $^{99m}$Tc/Re complex as a potential dual-modality imaging probe: synthesis, photophysical properties, cytotoxicity and cellular imaging investigations," *Dalton Transactions* 2014, 43 439-450, DOI: 10.1039/c3dt51968f, www.rsc.org/dalton.

(Continued)

*Primary Examiner* — Michael G. Hartley
*Assistant Examiner* — Jagadishwar R Samala
(74) *Attorney, Agent, or Firm* — Kilpatrick Townsend & Stockton LLP

(57) ABSTRACT

Multinuclear complexes and methods for preparing them are provided. The discrete multinuclear complexes include a one or more transition metals and a radioisotope having the same coordination geometry as the transition metal. A bridging ligand is coordinated to the transition metal and the radioisotope to link the transition metal and the radioisotope and pendent ligands are coordinated to each of the transition metal and the radioisotope to stabilise the complex. The multinuclear complexes may include a radioisotope or radioelement that can be detected by medical equipment and may find use in therapy and/or the diagnosis of disease in patients.

18 Claims, 4 Drawing Sheets

(56) References Cited

OTHER PUBLICATIONS

Gorschkov, et al., "Synthesis of [Tc(CO)$_3$(H$_2$O)$_3$]$^+$ Ion and Study of Its Reaction with Hydroxyl Ion in Aqueous Solutions," *Radiochemistry, vol. 42, No. 3, 2000. pp. 231-135. Translated from Radiokhimiya, vol. 42, No. 3. 2000, pp. 213-217. Original Russian Text Copyright.*
John Baldas, et al., "Synthesis and Structure of Di-p-OxO Nitridotechnetium(v1) Dimers and a Monomeric Nitridotechnetium(v) Mixed-ligand Complex", J. Chem. Soc. Dalton Trans, Jan. 1, 1992, XP55566923, Retrieved from the Internet: URL:https://pubs.rsc.org/en/content/articlepdf/1992/dt/dt9920002845 the whole document.
Karen E. Linder et al., "Neutral, seven-coordinate dioxime complexes of technetium (III): synthesis and characterization", Inorganic Chemistry, vol. 29, No. 13, Jun. 1, 1990, pp. 2428-2434, XP55566905, Easton, US ISSN: 0020-1669, DOI: 10.1021/ic00338a009 99TC(oxime)3(mu-OH)SnC13; the whole document.
Lim et al., Pyridine-ter-Nitrogen-Phenol Ligands: N,N,O-Type Tripodal Chelates for the [M(CO)$_3$]$^+$ Core (M = Re, Tc) *Inorganic Chemistry* 2008, 47, 1337-1345, 10 pages.
Miroslavov et al., "Synthesis and Properties of $^{99}$Tc(I) and $^{99m}$Tc(I) Hexacarbonyl in Aqueous Solutions," *ISSN 1066-3622. Radiochemistry, 2009, vol. 51, No. 2, pp. 124-131* DOI: 10.1134/S1066362209020040.
Schöster et al., "Contribution to the coordination chemistry of technetium II. Complexes of technetium(I) with selected ligands containing N, O and S donor atoms," *German Cancer Research Centre, Department of Radiochemistry, Im Neuenheimer Feld 280. D-69120 Heidelberg, Germany* (Received Sep. 24, 1996), 7 pages.
Syed Qaiser Shah et al., "Synthesis of $^{99m}$Tc(CO)$_3$_ Pazufloxacin Dithiocarbamate Complex and Biodistribution in Experimentally Induced Infection in Female Nude Mice," *Synthesis and Reactivity in Inorganic and Metal-Organic Chemistry*, 42:190-195, 2012.
Takayama et al., "Phenoxo-Bridged Dimeric Structure of Technetium(I) Tricarbonyl Complex with Schiff Base Ligand," *Journal of Nuclear and Radiochemical Sciences, vol. 6, No. 3, pp. 149-152, 2005.*
U.S. Appl. No. 16/957,000, filed Jun. 22, 2020, Restriction Requirement dated Jan. 19, 2021, all pages.
U.S. Appl. No. 16/957,000, filed Jun. 22, 2020, Non-Final Rejection dated Apr. 19, 2021, all pages.
Notice of Reasons for Rejection for Application No. JP 2020-530644 dated Jun. 23, 2021 8 pages.

* cited by examiner

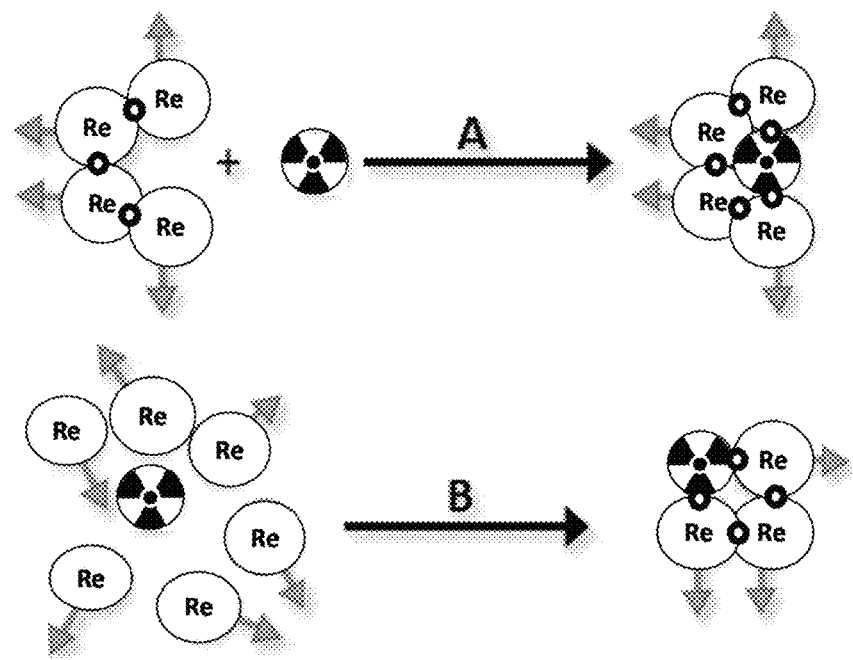
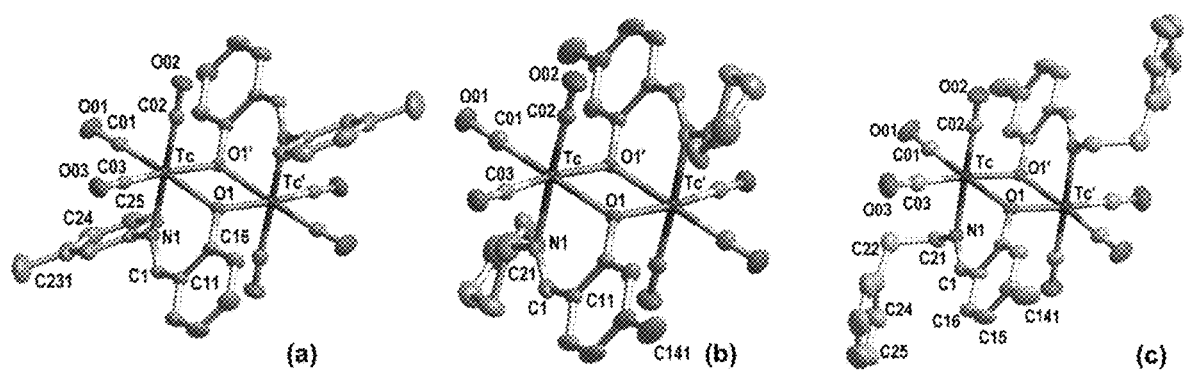
Figure 1
Figure 2

US 11,690,923 B2

MULTINUCLEAR COMPLEXES AND THEIR PREPARATION

CROSS-REFERENCE(S) TO RELATED APPLICATIONS

This application is a divisional of U.S. patent application Ser. No. 16/957,000, filed Jun. 22, 2020, which is a U.S. National Stage of International Application No. PCT/IB2018/60506, filed Dec. 21, 2018, which claims priority from South African provisional patent application number 2017/08729 filed on 21 Dec. 2017, the entire disclosures of which are hereby incorporated by reference here in their entireties.

FIELD OF THE INVENTION

This invention relates to multinuclear complexes and methods of preparing such multinuclear complexes. In particular, the invention relates to multinuclear transition metal complexes or clusters including a radionuclide or radioelement of the same or homologous elements.

BACKGROUND TO THE INVENTION

Research in medicinal inorganic chemistry is dominated by mononuclear organometallic complexes or coordination compounds. Their mode of action is often metal-based as in the case of cisplatin, for example. Some mononuclear complexes have ligand-based reactivity, whereas other mononuclear complexes are designed for biological recognition of the entire complex structure according to its 3D-space occupation. For biological recognition, the complex is "chemically innocent" and designed to bind to specific receptors. The topology of such mononuclear complexes and the functional groups mimic pharmaceutical lead structures of known activity as in the case of ferrocifen, ferroquine or protein kinase inhibitors of the staurosporine type, for example (G. Jaouen, A. Vessieres, S. Top, Chem. Soc. Rev. 2015, 44, 8802-8817; E. Hillard, A. Vessieres, L. Thouin, G. Jaouen, C. Amatore, Angew. Chem. Int. Edit 2006, 45, 285-290; S. Top, A. Vessieres, P. Pigeon, M. N. Rager, M. Huche, E. Salomon, C. Cabestaing, J. Vaissermann, G. Jaouen, Chembiochem 2004, 5, 1104-1113; D. Dive, C. Biot, Chemmedchem 2008, 3, 383-391; M. Navarro, W. Castro, C. Biot, Organometallics 2012, 31, 5715-5727; F. Dubar, C. Slomianny, J. Khalife, D. Dive, H. Kalamou, Y. Guerardel, P. Grellier, C. Biot, Angew. Chem. Int. Ed. 2013, 52, 7690-7693; S. Blanck, J. Maksimoska, J. Baumeister, K. Harms, R. Marmorstein, E. Meggers, Angew. Chem. Int. Edit. 2012, 51, 5244-5246).

Most of these metal-containing drugs are based on group 8, 9 or 10 elements (A. C. Komor, J. K. Barton, J. Am. Chem. Soc. 2014, 136, 14160-14172). Complexes of group 7 transition metals, particularly of the manganese triad involving the elements Mn, Tc and Re, are rarely investigated. It has been said that the chemistry of such complexes is not explored to a sufficient extent, in particular with respect to rhenium complexes (G. Gasser, N. Metzler-Nolte, Curr. Opin. Chem. Biol. 2012, 16, 84-91; A. Leonidova, G. Gasser, ACS Chem. Biol. 2014, 9, 2180-2193). Rhenium has two β-radiation emitting radionuclides, namely rhenium-186 ($^{186}$Re) and rhenium-188 ($^{188}$Re) used in medicine for targeted radiation therapy. Radiopharmaceuticals labelled with $^{186,188}$Re are known. It has also been shown that peptides or antibodies can be labelled with $^{188}$Re.

Like rhenium and manganese, technetium (Tc) is a group 7 element. Technetium-99m ($^{99m}$Tc) is a metastable nuclear isotope of technetium-99 ($^{99}$Tc), which is itself an isotope of Tc. $^{99m}$Tc is the most commonly used medical radioisotope. It is used as a medical tracer as it mainly emits gamma rays with a photon energy of 140 keV, which is readily detected by medical equipment in diagnostic procedures. Technetium-99m has a physical half-life of approximately six hours and a biological half-life of approximately one day. Technetium-99m decays to technetium-99 with a half-life of 211,000 years. Due to its short half-life, technetium-99m is produced locally at hospitals in generators from the decay of molybdenum-99. Only small concentrations in the nanomolar range (about $10^{-8}$-$10^{-6}$ M) are produced.

Cytotoxic, rhenium- or manganese-based mononuclear complexes, can be administered in combination with mononuclear complexes of $^{99m}$Tc as molecular imaging agents of identical structure to find use in molecule-based theranostics. For example, theranostics involves the use of macroscopic amounts of rhenium complexes for therapy and microscopic amounts of $^{99m}$Tc homologues for diagnosis. Both rhenium and technetium have low valences and form highly robust complexes. This has been showcased by the use of these complexes with carbonic anhydrase inhibitors and mitochondria targeting agents (D. Can, B. Spingler, P. Schmutz, F. Mendes, P. Raposinho, C. Fernandes, F. Carta, A. Innocenti, I. Santos, C. T. Supuran, R. Alberto, Angew. Chem. Int. Edit. 2012, 57, 3354-3357; S. Imstepf, V. Pierroz, R. Rubbiani, M. Felber, T. Fox, G. Gasser, R. Alberto, Angew. Chem. Int. Edit. 2016, 55, 2792-2795).

Generally, the use of multinuclear complexes or coordination compounds in medicinal inorganic chemistry is uncommon. Only polyoxometalates (POMs) have been studied for their application in nanomedicine (C. Yvon, A. J. Surman, M. Hutin, J. Alex, B. O. Smith, D. L. Long, L. Cronin, Angew. Chem. Int. Ed. 2014, 53, 3336-3341).

The lack of interest in multinuclear complexes may be due to their complex synthesis and in vivo behaviour. Apart from the POMs, multinuclear complexes have been reported, mainly with $Rh_2^{II}$ species exhibiting a Rh—Rh single bond (L. E. Joyce, J. D. Aguirre, A. M. Angeles-Boza, A. Chouai, P. K. L. Fu, K. R. Dunbar, C. Turro, Inorg. Chem. 2010, 49, 5371-5376; N. I. Shtemenko, H. T. Chifotides, K. V. Domasevitch, A. A. Golichenko, S. A. Babiy, Z. Y. Li, K. V. Paramonova, A. V. Shtemenko, K. R. Dunbar, J. Inorg. Biochem. 2013, 129, 127-134; H. T. Chifotides, K. R. Dunbar, Acc. Chem. Res. 2005, 38, 146-156.), and supramolecular Ru-arene complexes (a) E. Orhan, A. Garci, B. Therrien, Inorg. Chim. Acta 2017, 461, 78-83; E. Orhan, A. Garci, T. Riedel, M. Soudani, P. J. Dyson, B. Therrien, J. Organomet. Chem. 2016, 803, 39-44; E. Orhan, A. Garci, T. Riedel, P. J. Dyson, B. Therrien, J. Organomet. Chem. 2016, 815-816, 53-58; F. F. Li, J. G. Collins, F. R. Keene, Chem. Soc. Rev 2015, 44, 2529-2542).

As used herein, the term "multinuclear complex" refers to discrete polynuclear metal complexes or coordination compounds in which two or more metal-cations are bridged by a single coordinating atom, such as an oxygen for example, which may belong to a larger ligand system.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention, there is provided a multinuclear complex comprising:

a transition metal;
a radioisotope of the same coordination number as the transition metal;
a bridging ligand coordinated to the transition metal and the radioisotope to link the transition metal and the radioisotope; and
pendent ligands coordinated to each of the transition metal and the radioisotope.

Further features provide for the radioisotope to be an isotope of a transition metal or an isotope of an element of the same group in the periodic table as the transition metal; for the radioisotope to be an isotope of the elements of group 7 of the periodic table; for the radioisotope to be technetium-99m ($^{99m}$Tc), rhenium-186 ($^{186}$Re) or rhenium-188 ($^{188}$Re); for the transition metal to be selected from the group consisting of manganese (Mn), technetium (Tc) and rhenium (Re); for when the transition metal is rhenium, it to be β-radiation emitting isotopes of rhenium, rhenium-186 ($^{186}$Re) or rhenium-188 ($^{188}$Re) and when the transition metal is technetium, for it to be the technetium-99 ($^{99}$Tc) isotope; and for the transition metal and the radioisotope to each have a coordination number of six and octahedral coordination geometry in the multinuclear complex.

A yet further feature provides for the multinuclear complex to be a dinuclear complex represented by the molecular formula [$^{99m}$TcM(μ$_2$-L)$_2$(CO)$_6$],
wherein
M is Mn, Re or Tc, and
μ$_2$-L is a bidentate bridging ligand having at least two coordinating atoms independently selected from the group consisting of an oxygen atom, a sulphur atom, a selenium atom, a nitrogen atom, a carbon atom and a phosphorus atom, wherein one of the coordinating atoms of the bidentate ligand coordinates to both $^{99m}$Tc and M as a bridging coordinating atom and the other coordinating atom of the same bidentate ligand coordinates to one of $^{99m}$Tc or M.

A still further feature provides for the dinuclear complex to have anti or syn ligand geometry.

Still further features provide for the bidentate ligand (μ$_2$-L) to be a Schiff base chelator; and for the dinuclear complex to have the general formula (I):

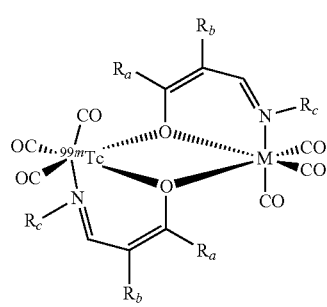

(I)

wherein
M is Mn, Re or Tc,
$R_a$, $R_b$ and $R_c$ are each independently a hydrogen, an optionally substituted C1-C10 linear or branched alkyl, an optionally substituted aryl, an optionally substituted heteroaryl, an optionally substituted poly(aryl), an optionally substituted poly(heteroaryl), an optionally substituted C5-C10 carbocyclyl or an optionally substituted heterocyclyl group and wherein $R_a$, $R_b$ and $R_c$ each optionally include one or more heteroatoms selected from the group consisting of an oxygen, nitrogen, sulphur, selenium, or halogen atom,
or $R_a$ and $R_b$ together is an optionally substituted cyclic aromatic hydrocarbon, an optionally substituted aromatic heterocycle, an optionally substituted polycyclic aromatic hydrocarbon, an optionally substituted polycyclic aromatic heterocycle, an optionally substituted cyclic or polycyclic hydrocarbon or an optionally substituted heterocycle or polyheterocycle,
or $R_a$, $R_b$ and $R_c$ together is an optionally substituted polycyclic aromatic hydrocarbon, an optionally substituted polycyclic aromatic heterocycle, an optionally substituted polycyclic hydrocarbon, or an optionally substituted polyheterocycle.

A further feature provides for the dinuclear complex to have the general formula (II):

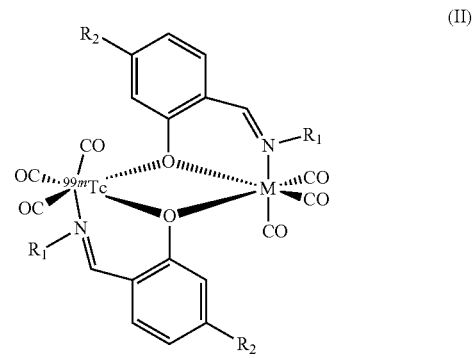

(II)

wherein M is Mn, Re or Tc, $R_1$ is an m-toluene group, a cyclopentane group, an ethylbenzene group or a bioactive or targeting moiety or a biological active functionality of known affinity for specific receptors and $R_2$ is hydrogen, a methyl group or a bioactive or targeting moiety or a biological active functionality of known affinity for specific receptors.

A yet further feature provides for the dinuclear complex to have the general formula (III):

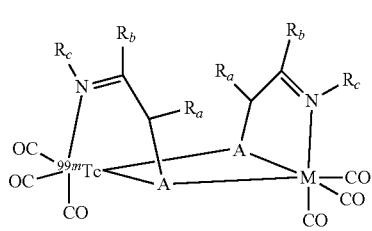

(III)

wherein
M is Mn, Re or Tc,
A is oxygen, sulfur or selenium;
$R_a$, $R_b$ and $R_c$ are each independently a hydrogen, an optionally substituted C1-C10 linear or branched alkyl, an optionally substituted aryl, an optionally substituted heteroaryl, an optionally substituted poly(aryl), an optionally substituted poly(heteroaryl), an optionally substituted C5-C10 carbocyclyl or an optionally substituted heterocyclyl group and wherein $R_a$, $R_b$ and $R_c$ each optionally include one or more heteroatoms selected from the group consisting of an oxygen, nitrogen, sulphur, selenium, or halogen atom, or $R_a$ and $R_b$ together is an optionally substituted cyclic aromatic hydrocarbon, an optionally substituted aromatic heterocycle, an optionally substituted polycyclic aromatic hydrocarbon, an optionally substituted polycyclic aromatic heterocycle, an optionally substituted cyclic or polycyclic hydrocarbon or an optionally substituted heterocycle or polyheterocycle, or $R_a$, $R_b$ and $R_c$ together is an optionally substituted polycyclic aromatic hydrocarbon, an optionally substituted polycyclic aromatic heterocycle, an optionally substituted polycyclic hydrocarbon, or an optionally substituted polyheterocycle.

Still further features provide for the halogen to be selected from the group consisting of fluorine, chlorine, bromine and iodine; for the polycyclic aromatic hydrocarbon to be selected from the group consisting of naphthalene, biphenyl, anthracene and phenanthrene; for a pendent functional group on the aromatic structure of the polycyclic aromatic hydrocarbon to include one or more hetero atoms; for the heteroatoms to be selected from the group consisting of oxygen, nitrogen, sulphur, selenium and phosphorus; and for the pendent functional group to be in the form of a monocyclopentadienyl or a bis-cyclopentadienyl entity.

A further feature provides for the bidentate ligand, more specifically one or more of $R_a$, $R_b$ or $R_c$ alone or together to be functionalized with a bioactive or targeting moiety, preferably a biologically active functionality of known affinity for a selected receptor.

Yet further features provide for the bidentate ligand ($\mu_2$-L) to be a quinoline-based chelator; and for the multinuclear complex to be a dinuclear complex of the general formula (IV)

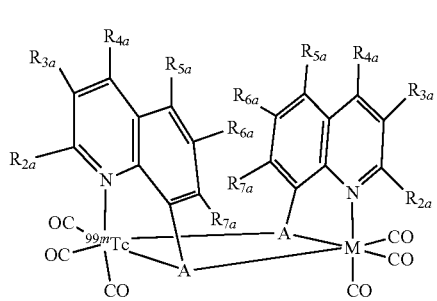

(IV)

wherein

M is Mn, Re or Tc;

A is oxygen, sulfur or selenium; and $R_{2a}$ to $R_{7a}$ are each independently a hydrogen, halogen, nitro, nitrile, amine, carboxylate, aldehyde, an optionally substituted C1-C10 linear or branched alkyl, an optionally substituted aryl, an optionally substituted heteroaryl, an optionally substituted poly(aryl), an optionally substituted poly(heteroaryl), an optionally substituted C5-C10 carbocyclyl or an optionally substituted heterocyclyl group and wherein $R_{2a}$ to $R_{7a}$ each optionally include one or more heteroatoms selected from the group consisting of an oxygen, nitrogen, sulphur, selenium, or halogen atom, or $R_{2a}$ to $R_{7a}$ together is an optionally substituted polycyclic aromatic hydrocarbon, an optionally substituted polycyclic aromatic heterocycle, an optionally substituted polycyclic hydrocarbon, or an optionally substituted polyheterocycle.

A still further feature provides for $R_{2a}$-$R_{7a}$ each independently to be a bioactive or targeting moiety, preferably a biologically active functionality of known affinity for a specific receptor.

A further feature provides for a trinuclear complex with a generally linear structure and the general formula $[^{99m}TcM_2O_2(\mu\text{-L})_2(LL)_6]$ wherein M is Mn, Re or Tc;

$\mu L$ is a bridging ligand selected from oxides ($O^{2-}$) or sulphides ($S^{2-}$); and LL is a bidentate pendant ligand separately coordinated to each of $^{99m}Tc$ and M and having at least two coordinating atoms independently selected from the group consisting of an oxygen atom, a sulphur atom, a selenium atom, a nitrogen atom, a carbon atom and a phosphorus atom.

Yet a further feature provides for the trinuclear complex to have the general formula (V):

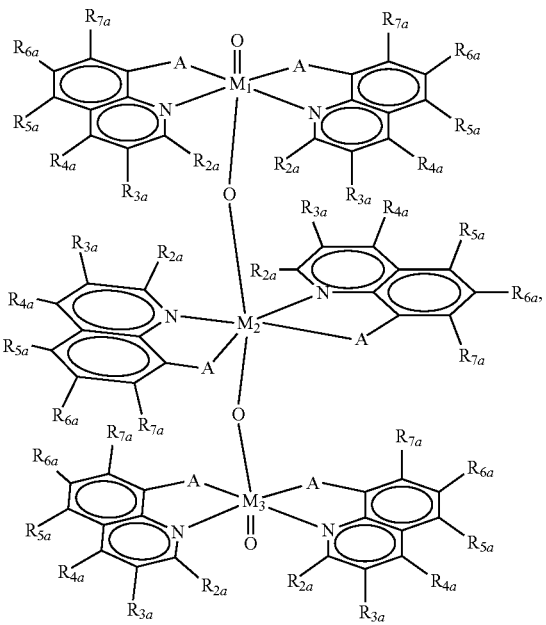

(V)

wherein at least one of $M_1$, $M_2$ or $M_3$ is $^{99m}Tc$ and the remaining metal centres of $M_1$, $M_2$ or $M_3$ are Mn, Re or Tc or any combination thereof;

A is an oxygen, sulfur or selenium atom; and $R_{2a}$ to $R_{7a}$ are as defined above.

A still further feature provides for $R_{2a}$ to be an amino group (—NH$_2$) and $R_{3a}$ to $R_{7a}$ to be hydrogen; or $R_{2a}$ to $R_{4a}$ and $R_{6a}$ to be hydrogen and $R_{5a}$ and $R_{7a}$ to be chlorine and; or $R_{2a}$ to $R_{6a}$ to be hydrogen and $R_{7a}$ to be a thiol group (—SH).

Further features provide for the multinuclear complex to be a tetranuclear complex represented by the molecular formula $[^{99m}TcM_3(L)_4(CO)_{12}]$, wherein M is Mn, Re or Tc, and L is a bridging ligand having a coordinating atom selected from the group consisting of an oxygen atom, a sulfur atom, and a selenium atom.

A further feature provides for the tetranuclear complex to have a cubane structure and the general formula (VI):

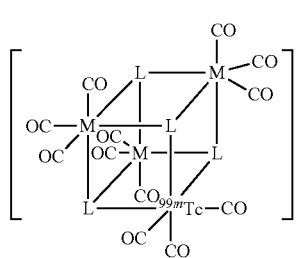

(VI)

wherein M is Mn, Re or Tc and L is a monodentate bridging ligand having a coordinating atom selected from the group consisting of an oxygen atom, a sulfur atom, and a selenium atom.

Further features provide for the bridging ligands (L) to be selected from the group consisting of hydroxides (OH$^-$), thiols (SH$^-$), optionally functionalised C1-C10 alkoxides, optionally functionalised C1-C10 thiolates and optionally functionalised C1-C10 selenolates; and for the C1-C10 alkoxides, C1-C10 thiolates and C1-C10 selenolates to be functionalised with a bioactive or targeting moiety.

A yet further feature provides for the tetranuclear complex to have the molecular formula [$^{99m}$TcRe$_3$($\mu_3$-OH)$_4$(CO)$_{12}$] and the structure (VII):

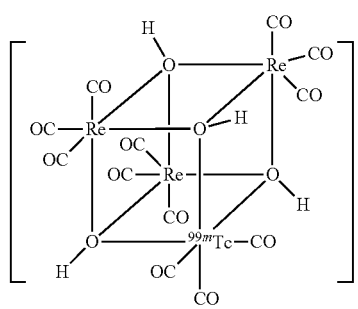

(VII)

In accordance with a second aspect, there is provided a method of preparing a multinuclear complex by self-assembly comprising:

mixing a multinuclear or mononuclear precursor complex of a transition metal with a mononuclear complex that includes a radioisotope of the same coordination number as the transition metal in a selected solvent or solvent system.

Further features of this aspect provide for the multinuclear or mononuclear precursor complex of a transition metal to be anionic and the mononuclear complex that includes the radioisotope to be cationic in solution; for the precursor complex and the complex that includes the radioisotope to have octahedral coordination geometry; for the radioisotope to be an isotope of a transition metal or an isotope of an element of the same group in the periodic table as the transition metal; for the radioisotope to be technetium-99m ($^{99m}$Tc); and for the transition metal to be selected from the group consisting of manganese, technetium and rhenium.

Yet further features provide for the mononuclear precursor complex to have the general molecular formula fac-[M(X)$_3$(CO)$_3$]$^{2-}$ in solution, wherein M is Mn, Re or Tc, X is Br when M is Re and X is Cl when M is Tc and for the mononuclear complex including a radioisotope to have the general molecular formula [$^{99m}$Tc(Y)$_3$(CO)$_3$]$^+$ in solution, wherein Y is as neutral ligand, preferably water (OH$_2$) or a solvent molecule; for the solvent to be water, alcohol, acetonitrile, acetone or dimethylsulfoxide, preferably acetonitrile, and for the mixing to occur in the presence of the abovementioned bidentate ligand ($\mu_2$-L) to form the dinuclear complex as defined above; for the mixing step to be carried out in the presence of excess base, preferably triethylamine; and for the mixing step to be carried out at elevated temperatures; for the mixing step to be carried out at between about 60° C. and 90° C., preferably about 80° C. for 3 hours.

Still further features provide for the preparation of a tetranuclear complex as defined above in one step by adding the mononuclear precursor complex of the general molecular formula, fac-[M(Z)$_3$(CO)$_3$]$^+$, wherein M is Mn, Re or Tc and Z is a protonated monodentate bridging ligand (H-L), to a solution of the mononuclear complex of the general molecular formula fac-[$^{99m}$Tc(Z)$_3$(CO)$_3$]$^+$, wherein Z is a protonated monodentate bridging ligand (H-L) and mixing the resultant solution; and for the pH of the solution of the mononuclear complex of the general molecular formula fac-[$^{99m}$Tc(Z)$_3$(CO)$_3$]$^+$ to be adjusted to be mildly acidic, preferably to be about 5, prior to adding the mononuclear precursor complex to it.

A further feature provides for Z to be OH$_2$ and for the solution to be an aqueous solution.

Further features provide for the preparation of a tetranuclear complex as defined above by preassembly of a multinuclear precursor complex in the form of an anionic trinuclear complex that leaves a vertex for the coordination of the complex including the radioisotope; for the trinuclear complex to have the general molecular formula [M$_3$($\mu_2$-L)$_3$($\mu_3$-L)(CO)$_9$]$^-$, wherein M is Mn, Re or Tc and $\mu_2$-L is a monodentate ligand as defined above coordinated to two metal centres and $\mu_3$-L is a monodentate ligand as defined above coordinated to three metal centres; for the anionic trinuclear complex to be added to a solution of the mononuclear complex of the general molecular formula fac-[$^{99m}$Tc(Z)$_3$(CO)$_3$]$^+$, wherein Z is a protonated monodentate bridging ligand (H-L) of the tetranuclear complex, and for the resultant solution to be mixed; and for the pH of the solution to be adjusted to be mildly acidic, preferably to be about 5, prior to adding the trinuclear precursor complex to it.

A further feature provides for Z to be OH$_2$ and for the solution to be an aqueous solution.

In accordance with a third aspect of the invention, there is provided a pharmaceutical composition including a multinuclear complex as described above, together with a diluent, excipient or carrier.

An embodiment of the invention will now be described, byway of example only, with reference to the accompanying drawings.

BRIEF DESCRIPTION OF THE DRAWINGS

In the drawings:
FIG. 1 is a schematic showing two different strategies, pathway A and B, for forming multinuclear complexes with Re metal centres and a $^{99m}$Tc fragment serving as a radiolabel;
FIG. 2 is ORTEP diagrams of dinuclear complexes of $^{99}$Tc, [$^{99}$Tc$_2$($\mu_2$-O^N—R$_1$)$_2$(CO)$_6$](a) R$_1$=m-tol, R$_2$=H (1);

Figure 3:
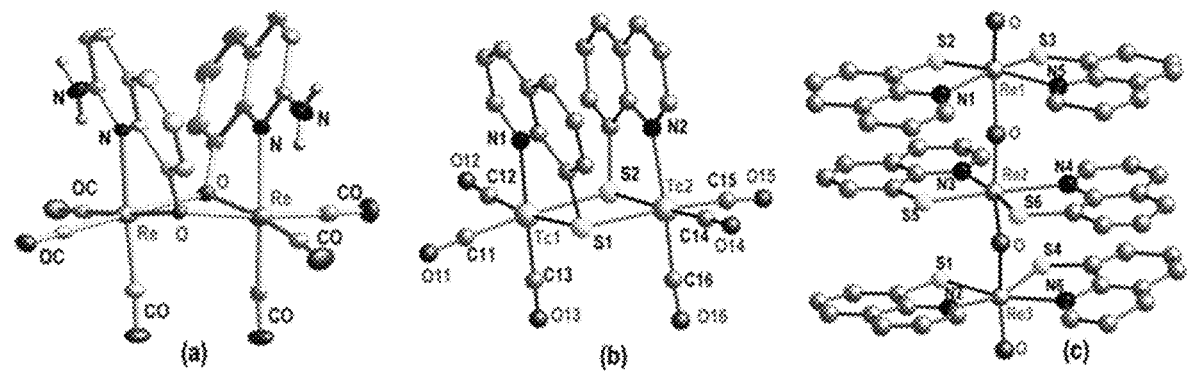
Figure 4:
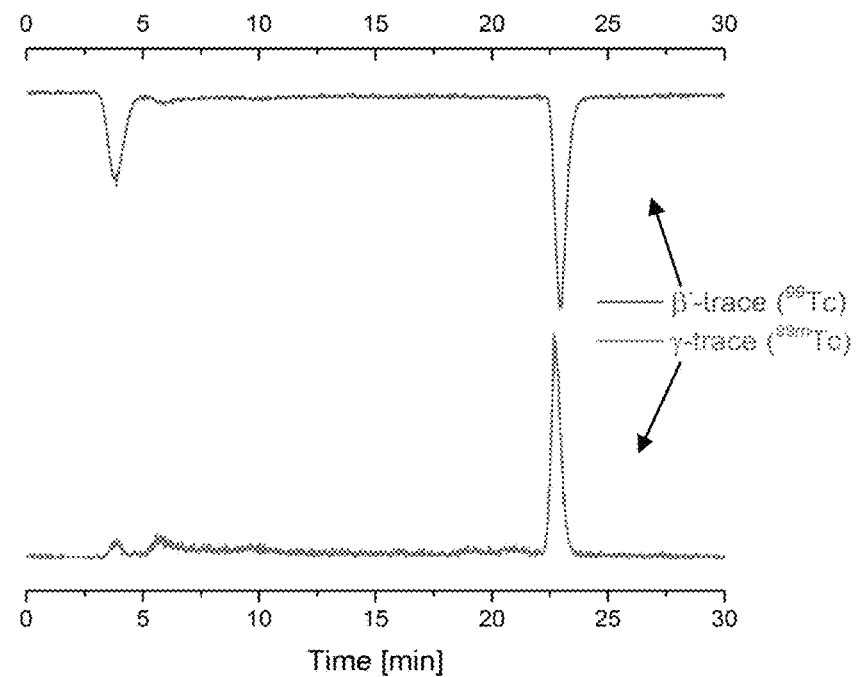
Figure 5:
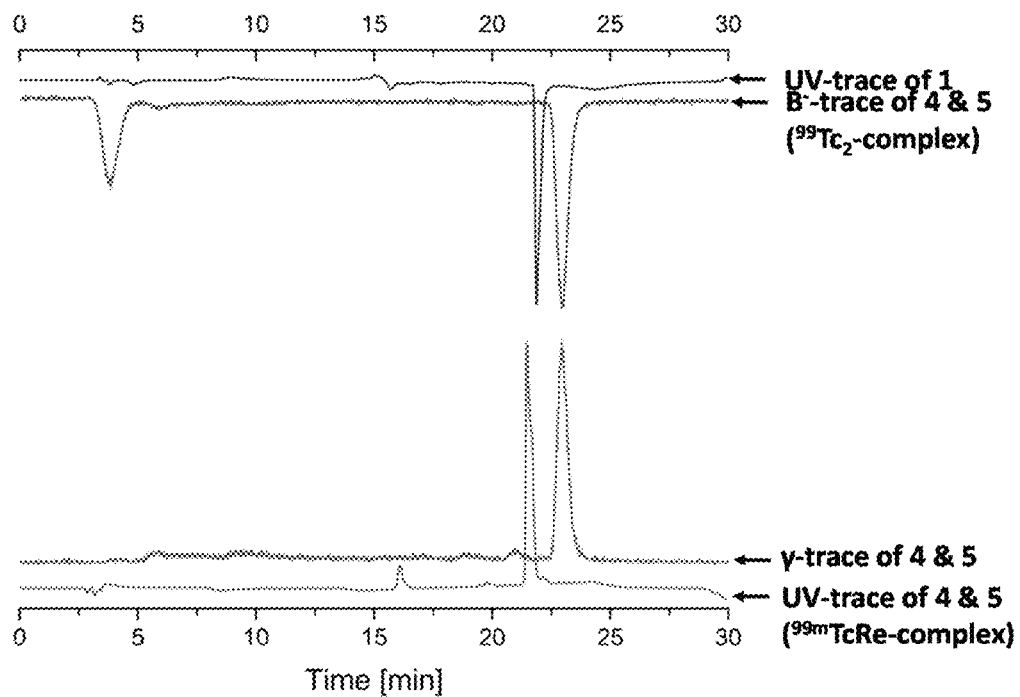
Figure 6:
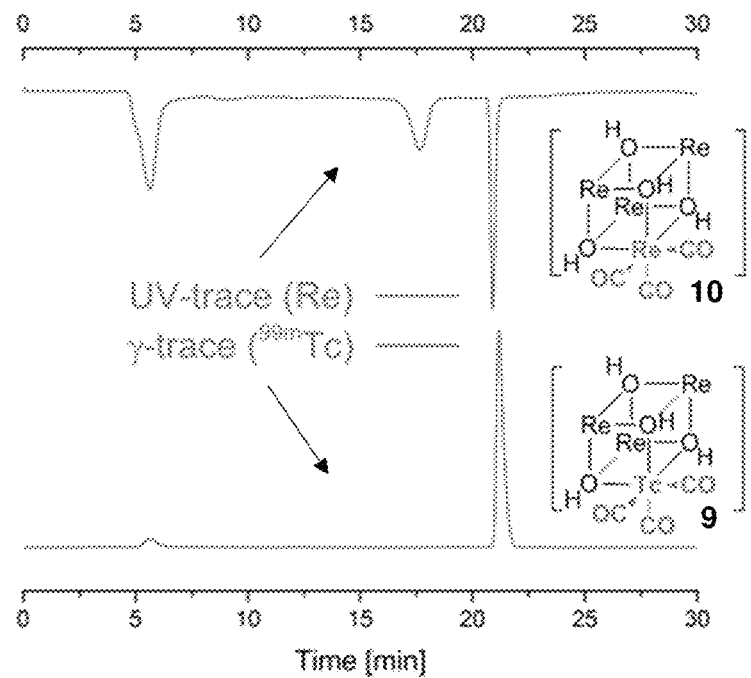
Figure 7:
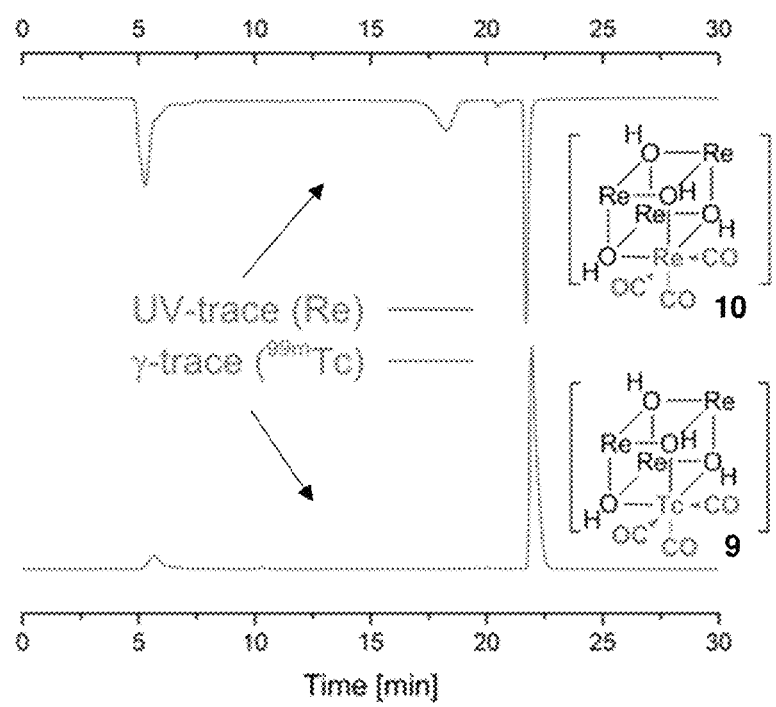

(b) $R_1$=cpent, $R_2$=Me (2); and (c) $R_1$=EtPh, $R_2$=Me (3) with the ellipsoids shown at a 50% probability level;

FIG. 3 is DIAMOND plots of model dinuclear complexes of (a) syn-$[^{99}Re_2(\mu_2\text{-}2Aox)_2(CO)_6]$ and (b) syn-$[^{99}Tc_2(\mu_2\text{-tox})_2(CO)_6]$, which was difficult to obtain in large amounts and are modelled currently on Re, and (c) the likely structure of trans,trans,trans-$[^{99m}TcRe_2O_2(\mu\_O)_2(LL)_6]$ modelled on trans,trans,trans-$[Re_3O_2(\mu\_O)_2(LL)_6]$;

FIG. 4 is a graph showing the Radio-High Performance Liquid Chromatography (radio-HPLC) $\beta^-$-trace of the dinuclear complex, $[^{99}Tc_2(\mu_2\text{-O}^\wedge N\text{-m-tol})_2(CO)_6]$ (1), and the $\gamma$-trace of the dinuclear complex, $[^{99}Tc^{99m}Tc(\mu_2\text{-O}^\wedge N\text{-m-tol})_2(CO)_6]$;

FIG. 5 is a graph showing HPLC traces of the crude reaction mixture for the preparation of $[^{99m}TcRe(\mu_2\text{-O}^\wedge N\text{-m-tol})_2(CO)_6]$ (5) containing mostly mononuclear Re complexes of the type fac-$[Re(O^\wedge N\text{-m-tol})(CO)_3(Sol)]$ (4) due to the large excess of rhenium present and the HPLC traces with UV/vis- and ($\beta^-$-detection of $[^{99}Tc_2(\mu_2\text{-O}^\wedge N\text{-m-tol})_2(CO)_6]$ (1);

FIG. 6 is a graph showing HPLC traces of $[^{99m}TcRe_3(\mu_3\text{-OH})_4(CO)_{12}]$ (9) and $[Re_4(\mu_3\text{-OH})_4(CO)_{12}]$ (10) formed via a trinuclear precursor complex in terms of pathway A, the respective traces measured with UV/vis detection for 10 and $\gamma$-detection for 9; and FIG. 7 is a graph showing HPLC traces of $[^{99m}TcRe_3(\mu_3\text{-OH})_4(CO)_{12}]$ (9) and $[Re_4(\mu_3\text{-OH})_4(CO)_{12}]$ (10) formed in one step via self-assembly of mononuclear precursors in terms of pathway B, the respective traces measured with UV/vis detection for 10 and $\gamma$-detection for 9.

DETAILED DESCRIPTION WITH REFERENCE TO THE DRAWINGS

A multinuclear organometallic complex or cluster including at least one transition metal centre of and at least one radioisotope metal centre with the same coordination geometry as the transition metal is provided. The complexes may include transition metals of group 7 in the periodic table such as manganese, technetium and rhenium. The transition metal centre(s) and radioisotope 25 metal centre(s) may have octahedral coordination geometry and are connected by suitable bridging ligands. The remaining coordination sites surrounding the transition metal centre(s) and radioisotope metal centre(s) are occupied by stabilising pendent ligands. Ligands that stabilise the system are inert ligands and ligands that are not easily substituted such as carbonyl (CO) ligands, oxo ($O^{2-}$) ligands or other suitable chelating ligands. If more labile pendent groups are included in the structure, it would induce the formation of polymeric structures rather than discrete complexes.

Various isomers of the multinuclear complexes described herein may be prepared. These may be structural isomers such as complexes in which the ligands have anti or syn geometry, constitutional isomers such as solvates and stereoisomers with ligand-based stereochemistry.

The multinuclear complexes are prepared by self-assembly in solution. The multinuclear complexes form by mixing a multinuclear cluster or mononuclear precursor complex of a transition metal with a mononuclear complex that includes a radioisotope of the same coordination number so as to have the same coordination geometry as the transition metal in a suitable solvent system and in the presence of selected ligands. The multinuclear or mononuclear precursor complex and the complex that includes a radioisotope may have octahedral coordination geometry. To form a multinuclear complex having a selected number of metal centres and a selected structure, a suitable bridging ligand may be added to the solution or may already be coordinated to the precursor transition complex and the radioisotope-containing complex. The solution must be at a selected pH to ensure coordination of the bridging ligands and to connect or self-assemble the precursor transition complex which may, for example, be anionic and the radioisotope-containing complex which may then be cationic in solution. An excess of the multinuclear or mononuclear precursor complex of a transition metal in solution drives the reaction forward so that multinuclear complexes that include the radioisotope form relatively rapidly together with complexes that do not include the radioisotope. The reaction rate is proportional to the square of the concentration ($conc^2$) of the excess precursor complex of the transition metal as per second order reaction kinetics.

The radioisotope may be an isotope of a transition metal element, a radioactive element, or an isotope of an element in the same group in the periodic table as the transition metal in the multinuclear complex. In certain embodiments, the transition metal may be Re or Tc and the radioisotope may be $^{99m}Tc$. When the metal is Re, it may be the radiotherapeutic $^{188}Re$ or $^{186}Re$ or a combination thereof in the same complex. In the event of the metal being Tc it may be the stable isotope $^{99}Tc$. This isotope does not find use as a tracer or in therapy though. Nevertheless, the multinuclear complex can include one or both of $^{188}Re$ and $^{186}Re$, in addition to $^{99}Tc$. Where the complex includes one or both of $^{188}Re$ or $^{186}Re$ and the radioisotope is $^{99m}Tc$, the single multinuclear complex has both therapeutic and diagnostic potential and thus may be applied in theranostics.

The multinuclear complex may be a dinuclear complex represented by the molecular formula $[^{99m}TcM(\mu_2\text{-L})_2(CO)_6]$, wherein M is manganese (Mn), rhenium (Re) or technetium (Tc) and any isotopes thereof (but not $^{99m}Tc$), and $\mu_2$-L is a bidentate bridging ligand having at least two coordinating atoms independently selected from the group consisting of an oxygen atom, a sulfur atom, a selenium atom, a nitrogen atom and a phosphorus atom. One of the coordinating atoms of the bidentate ligand, preferably an oxygen, sulfur or selenium atom, coordinates to both $^{99m}Tc$ and M as a bridging coordinating atom and the other coordinating atom, preferably a nitrogen or phosphorus atom of the same bidentate ligand coordinates to one of $^{99m}Tc$ or M.

The bidentate ligand may be specifically designed as a macro-ligand including a bioactive or targeting moiety. The bioactive moiety may be therapeutic to provide further therapy in addition to the radiotherapeutic metal centre. Alternatively, a bioactive, therapeutic moiety may be included in the multinuclear complex specifically if the metal centre itself is not therapeutic. The bidentate ligand may also include a diagnostic or biological recognition moiety for diagnosis or targeted therapy.

The bidentate ligand may be a Schiff base chelator and the dinuclear complex may have the general formula (I):

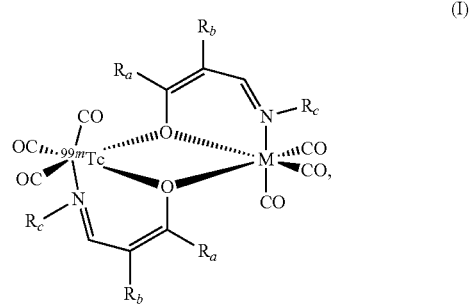

wherein

M is Mn, Re or Tc, $R_a$, $R_b$ and $R_c$ are each independently a hydrogen, an optionally substituted C1-C10 linear or branched alkyl, an optionally substituted aryl, an optionally substituted heteroaryl, an optionally substituted poly(aryl) such as a naphthalene, biphenyl, anthracene and phenanthrene, an optionally substituted poly(heteroaryl), an optionally substituted C5-C10 carbocyclyl or an optionally substituted heterocyclyl group, and wherein $R_a$, $R_b$ and $R_c$ each optionally include one or more heteroatoms selected from the group consisting of an oxygen, nitrogen, sulphur, selenium, or halogen atom such as a fluorine, chlorine, bromine and iodine, or $R_a$ and $R_b$ together is an optionally substituted cyclic aromatic hydrocarbon, an optionally substituted aromatic heterocycle, an optionally substituted polycyclic aromatic hydrocarbon such as a naphthalene, biphenyl, anthracene and phenanthrene, an optionally substituted polycyclic aromatic heterocycle, an optionally substituted cyclic or polycyclic hydrocarbon or an optionally substituted heterocycle or polyheterocycle, or $R_a$, $R_b$ and $R_c$ together is an optionally substituted polycyclic aromatic hydrocarbon such as a naphthalene, biphenyl, anthracene and phenanthrene, an optionally substituted polycyclic aromatic heterocycle, an optionally substituted polycyclic hydrocarbon, or an optionally substituted polyheterocycle.

In the event that $R_a$, $R_b$ and $R_c$ together or independently contains an aromatic ring, the aromatic structure or a pendent functional group may include one or more hetero atoms selected from the group consisting of oxygen, nitrogen, sulphur, selenium and phosphorus. The pendent functional group may also be in the form of a mono cyclopentadienyl with piano-stool geometry such as for example [CrCp(CO)$_3$)], or a bis-cyclopentadienyl with either bent geometry such as [ZrCp$_2$Cl$_2$], or with a sandwich geometry such as ferrocene ([FeCp$_2$], bis($\eta^5$-cyclopentadienyl)iron).

The chelator for the dinuclear Schiff base complex may be of the following general formula (Ia):

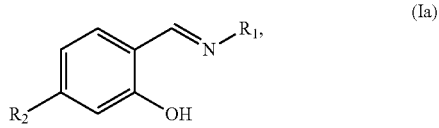

(Ia)

in which $R_1$ or $R_2$ or both $R_1$ and $R_2$ are bioactive or targeting moieties, preferably biologically active functionalities with known affinity for a selected biological receptors.

As proof of concept, multinuclear complexes with Schiff base chelators in which $R_1$ is an m-toluene group, a cyclopentane group, or an ethylbenzene group and $R_2$ a hydrogen or a methyl group have been prepared.

In particular, the dinuclear complex may have the general formula (II):

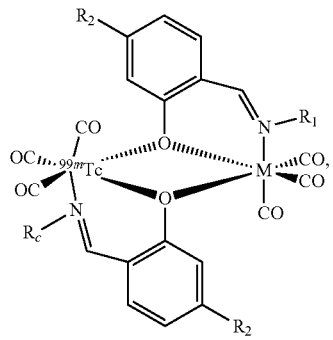

(II)

wherein M is Mn, Re or Tc and $R_1$ and $R_2$ are as defined with reference to general formula (Ia).

Alternatively, the dinuclear complex may have the general formula (III) and the ligands ($\mu_2$-L) may have either syn (illustrated in formula (III)) or anti symmetry relative to the $^{99m}T_c$-A-A-M plane,

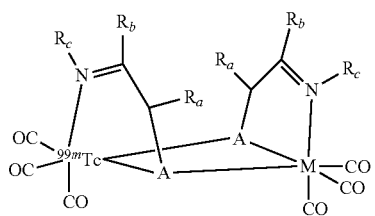

(III)

wherein

M is Mn, Re or Tc,

A is oxygen, sulfur or selenium;

$R_a$, $R_b$ and $R_c$ are each independently an optionally substituted C1-C10 linear or branched alkyl, an optionally substituted aryl, an optionally substituted heteroaryl, an optionally substituted poly(aryl) such as a naphthalene, biphenyl, anthracene and phenanthrene, an optionally substituted poly(heteroaryl), an optionally substituted C5-C10 carbocyclyl or an optionally substituted heterocyclyl group, and wherein $R_a$ $R_b$ and $R_c$ each optionally include one or more heteroatoms selected from the group consisting of an oxygen, nitrogen, sulphur, selenium, or halogen atom such as fluorine, chlorine, bromine and iodine, or $R_a$ and $R_b$ together is an optionally substituted cyclic aromatic hydrocarbon, an optionally substituted aromatic heterocycle, an optionally substituted polycyclic aromatic hydrocarbon such as a naphthalene, biphenyl, anthracene and phenanthrene, an optionally substituted polycyclic aromatic heterocycle, an optionally substituted cyclic or polycyclic hydrocarbon or an optionally substituted heterocycle or polyheterocycle, or $R_a$, $R_b$ and $R_c$ together is an optionally substituted polycyclic aromatic hydrocarbon such as a naphthalene, biphenyl, anthracene and phenanthrene, an optionally substituted polycyclic aromatic heterocycle, an optionally substituted polycyclic hydrocarbon, or an optionally substituted polyheterocycle.

A pendent functional group on the aromatic structure of the polycyclic aromatic hydrocarbon may include one or more hetero atoms selected from oxygen, nitrogen, sulphur, selenium and phosphorus. Alternatively, the pendent functional group may be in the form of a mono-cyclopentadienyl or a bis-cyclopentadienyl entity.

The dinuclear complex may be a syn complex in which the two bridging ligands ($\mu_2$-L) are cis to the $^{99m}$Tc-A-A-M plane, as indicated in formula (III), or an anti complex in which the two bridging ligands ($\mu_2$-L) are trans to the $^{99m}$Tc-A-A-M plane.

The chelator (Hquin) for the dinuclear quinoline complex may be of the following general formula (IIIa):

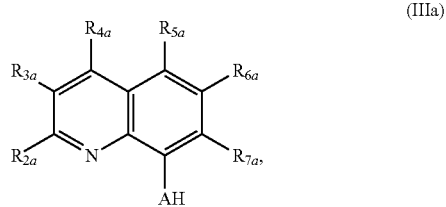

(IIIa)

in which

A is an oxygen, sulfur or selenium;

$R_{2a}$ to $R_{7a}$ are each independently a hydrogen, halogen, nitro, nitrile, amine, carboxylate, aldehyde, an optionally substituted C1-C10 linear or branched alkyl, an optionally substituted aryl, an optionally substituted heteroaryl, an optionally substituted poly(aryl), an optionally substituted poly(heteroaryl), an optionally substituted C5-C10 carbocyclyl or an optionally substituted heterocyclyl group and wherein $R_{2a}$ to $R_{7a}$ each optionally include one or more heteroatoms selected from the group consisting of an oxygen, nitrogen, sulphur, selenium, or halogen atom, or $R_{2a}$ to $R_{7a}$ together is an optionally substituted polycyclic aromatic hydrocarbon, an optionally substituted polycyclic aromatic heterocycle, an optionally substituted polycyclic hydrocarbon, or an optionally substituted polyheterocycle.

For example, $R_{2a}$ may be an amino group (—NH$_2$) and $R_{3a}$ to $R_{7a}$ hydrogens. Alternatively, $R_{2a}$ to $R_{4a}$ and $R_{6a}$ may be hydrogens and $R_{5a}$ and $R_{7a}$ chlorine atoms. In other embodiment, $R_{2a}$ to $R_{6a}$ are hydrogens and $R_{7a}$ is a thiol group (—SH). In preferred embodiments, $R_{2a}$ to $R_{7a}$ may each independently be a bioactive or targeting moiety or $R_{2a}$ to $R_{7a}$ may each independently be a biological active functionality of known affinity for specific receptors.

The dinuclear quinoline-based complex may have the general formula (IV)

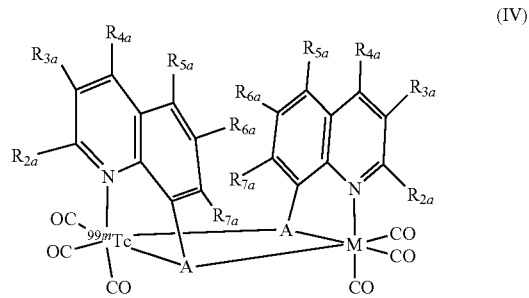

(IV)

wherein M, A and $R_{2a}$ to $R_{7a}$ are as defined above with reference to the general formula (IIIa) of the quinoline-based chelator.

The coordination geometry of the dinuclear complex (IV) may be syn, wherein the two bidentate bridging ligands ($\mu_2$-L) are cis to the $^{99m}$Tc-A-A-M plane, as indicated in the general formula (IV). Alternatively, the coordination geometry may be anti, wherein the two bridging ligands ($\mu_2$-L) are trans to the $^{99m}$Tc-A-A-M plane.

The dinuclear complexes may be prepared by mixing together the anionic, mononuclear metal complex, the cationic mononuclear $^{99m}$Tc complex and the bidentate ligand ($\mu_2$-L), such as the Schiff base chelator (Ia) or quinoline-based chelator (IIIa), in a solution, preferably in a polar solvent, more preferably an aprotic solvent of medium polarity such as acetonitrile. The absolute concentration of the precursor metal complex and the bidentate ligand governs the reaction. The precursor metal complex and bidentate ligand, typically present in a concentration range of about 0.01 to 0.03 mol/dm$^3$ are mixed with the $^{99m}$Tc complex typically having a concentration of $10^{-8}$ mol/dm$^3$. To deprotonate one of the coordinating groups of the bidentate ligand, i.e. to form the monovalent coordinating O-atom, S-atom or Se-atom, a strong base, such as triethylamine, is added to the solution before mixing it. The mixing may be done at elevated temperatures of between 60° C. and 90° C. for a selected period, preferably about 80° C. for 3 hours.

In this manner, the dincuclear complex of general formulae (II) and (IV) are self-assembled by mixing excess precursor metal complex of the general molecular formula fac-[M(X)$_3$(CO)$_3$]$^{2+}$, wherein M is Mn, Re or Tc, X is Br when M is Re and X is Cl when M is Tc, with the mononuclear complex including a radioisotope of the general molecular formula [$^{99m}$Tc(Y)$_3$(CO)$_3$]$^+$, wherein Y is as neutral ligand, preferably (OH$_2$), in the presence of the above described precursor bidentate ligand ($\mu_2$-L) and a base. Y may also be a coordinating solvent molecule such as methanol and other alcohols, acetonitrile, acetone and dimethylsulfoxide, provided that the reactants and products are soluble in such a solvent. When the reactants and products are dissolved, Y as a neutral ligand, rapidly exchanges with these solvent molecules.

The multinuclear complex may be a trinuclear complex with three metal centres and a generally linear structure. The trinuclear complex may have the general formula [$^{99m}$TcM$_2$O$_2$($\mu$_L)$_2$(LL)$_6$] in which M is Mn, Re or Tc; $\mu$L is a bridging ligand selected from the group consisting of oxides (O$^{2-}$) and sulphides (S$^{2-}$); and LL is a bidentate pendent ligand having at least two coordinating atoms independently selected from the group consisting of an oxygen atom, a sulphur atom, a selenium atom, a nitrogen atom, a carbon atom and a phosphorus atom, wherein both of the coordinating atoms of the bidentate ligand coordinates to either $^{99m}$Tc or M.

The trinuclear complex may have the general formula and structure (V):

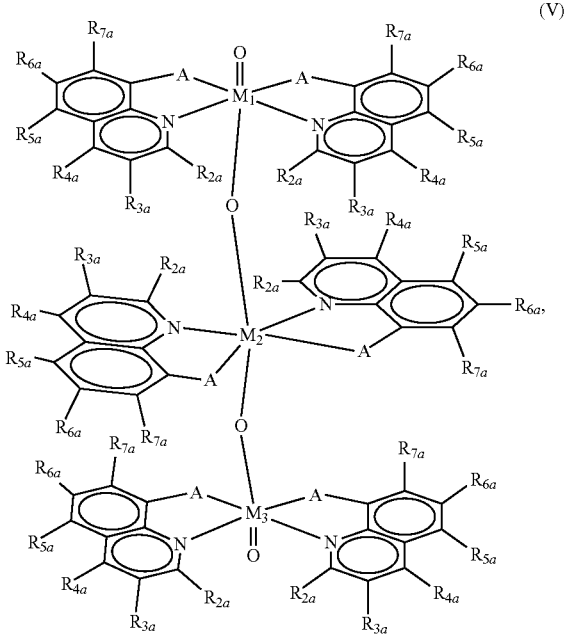

(V)

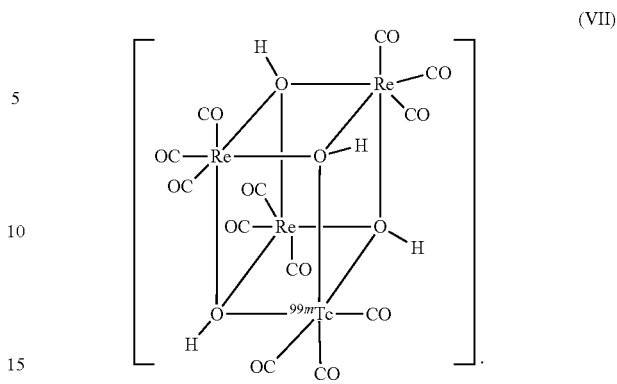

(VII)

wherein at least one of $M_1$, $M_2$ or $M_3$ is $^{99m}$Tc, and the remaining metal centres of $M_1$, $M_2$ or $M_3$ are Mn, Re or Tc or any combination thereof; A is an oxygen, sulfur or selenium atom; and $R_{2a}$-$R_{7a}$ are as defined above with reference to the general formula of the quinoline-based ligand (IIIa).

The multinuclear complex may also be a tetranuclear complex represented by the molecular formula $[^{99m}TcM_3(L)_4(CO)_{12}]$, wherein M is Mn, Re or Tc, and L is a monodentate ligand. The tetranuclear complex may have a monodentate ligand (L) that bridges three metal centres (M) or two metal centers and $^{99m}$Tc to form a cubane structure of the general formula (VI):

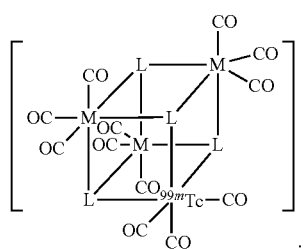

(VI)

The monodentate ligand (L) may have a coordinating atom selected from the group consisting of an oxygen atom, a sulfur atom, and a selenium atom. Accordingly, the monodentate ligand may be selected from the group consisting of hydroxides (OH⁻), thiols (SH⁻), optionally functionalised C1-C10 alkoxides, optionally functionnalised C1-C10 thiolates and optionally functionalised C1-C10 selenolates. The C1-C10 alkoxides, C1-C10 thiolates and C1-C10 selenolates may also be functionalised with a bioactive or targeting moiety as previously described with reference to the bidentate ligands of the dinuclear complexes.

The tetranuclear complex may have the molecular formula $[^{99m}TcRe_3(\mu_3\text{-OH})_4(CO)_{12}]$ and the following structure (VII):

A multinuclear complex with more than two metal centres may be prepared by one of two principal pathways schematically illustrated in FIG. 1:
A) the preparation of an incomplete fragment of the final, multinuclear complex followed by introduction of the radioisotope complex (the radiolabel) in a second step (pre-assembly strategy, pathway A in FIG. 1); or
B) the combination of all of the components to prepare the multinuclear complex in one step (self-assembly strategy, pathway B in FIG. 1).

Tetranuclear Complex Via Pathway A:

A tetranuclear complex may, for example, be prepared by preassembly of a multinuclear precursor complex as per pathway A, such as an anionic trinuclear complex that has a vertex available for the coordination of the complex including the radioisotope. The trinuclear complex is anionic and may have the general molecular formula $[M_3(\mu_2\text{-L})_3(\mu_3\text{-L})(CO)_9]^-$, wherein M is Mn, Re or Tc and $\mu_2$-L is a monodentate ligand coordinated to two metal centres and $\mu_3$-L is a monodentate ligand coordinated to three metal centres. The monodentate ligands, $\mu_2$-L and $\mu_3$-L, may be hydroxides (OH⁻), thiols (SH⁻), optionally functionalised C1-C10 alkoxides, optionally functionalised C1-C10 thiolates and optionally functionalised C1-C10 selenolates which are present in the precursor mononuclear complexes (fragments) that the trinuclear complex is built from stepwise.

An excess of anionic trinuclear complex, typically about 0.005-0.02 mol/dm³, may be added to a solution of the precursor radiolabel complex, i.e. the cationic, mononuclear complex of the general molecular formula fac-$[^{99m}Tc(Z)_3(CO)_3]^+$, wherein Z is a protonated monodentate bridging ligand (H-L) of the resultant tetranuclear complex. The solvent is preferably a polar solvent. It should be noted that whilst fac-$[^{99m}Tc(Z)_3(CO)_3]^+$ is in solution, Z may also be a coordinating solvent molecule, provided that the complex and eventual products formed are soluble in the solvent. Solvents such as methanol and other alcohols, acetonitrile, acetone and dimethylsulfoxide may be used, which results in a rapid replacement of Z by the relevant solvent molecule.

To form a complex with the general molecular formula $[^{99m}TcM_3(\mu_3\text{-OH})_4(CO)_{12}]$, in which M is Mn, Re or Tc and the bridging ligand (L) is a hydroxide, the "leaving" ligand, Z, is water coordinated via the oxygen-atom (OH₂) and the solution of the radiolabel complex (radioisotope containing complex) is preferably an aqueous solution. The pH of the aqueous solution of the precursor radiolabel complex, fac-$[^{99m}Tc(OH_2)_3(CO)_3]^+$, is adjusted to be mildly acidic, preferably to be about 5, prior to the addition of the trinuclear complex to it. After the N₂ purged anionic trinuclear complex is added to the aqueous solution of the cationic radiolabel complex, self-assembly of the tetranuclear complex occurs quite rapidly, especially when the solution is stirred at elevated temperatures of 100° C., for example, for about 10 minutes.

Tetranuclear Complex Via Pathway B:

A tetranuclear complex can also be formed in one step by adding the mononuclear precursor complex of the general molecular formula, fac-[M(Z)$_3$(CO)$_3$]$^+$, wherein M is Mn, Re or Tc and Z is a protonated monodentate bridging ligand (H-L), to a solution of the mononuclear complex of the general molecular formula fac-[$^{99m}$Tc(Z)$_3$(CO)$_3$]$^+$ in which Z is the same as in the mononuclear precursor complex or is a coordinating solvent molecule, preferably in a polar solvent, and mixing the resulting solution. The complex fac-[M(Z)$_3$(CO)$_3$]$^+$ is added in excess of the radiolabel complex, fac-[$^{99m}$Tc(Z)$_3$(CO)$_3$]$^+$ which is only available in nanomolar concentration ranges. The complex, fac-[M(Z)$_3$(CO)$_3$]$^+$, is typically added to the solution in an amount of about 0.01-0.03 mol/dm$^3$.

To form the tetranuclear complex [$^{99m}$TcM$_3$(μ$_3$_OH)$_4$(CO)$_{12}$], in which M is Mn, Re or Tc and the bridging ligand is a hydroxide, the radiolabel complex is dissolved in an aqueous solution and Z is OH$_2$ so that the mixing and self-assembly occurs in the aqueous solution. The pH of the aqueous solution of the mononuclear complex of the general molecular formula fac-[$^{99m}$Tc(OH$_2$)$_3$(CO)$_3$]$^+$ may be adjusted to be mildly acidic, preferably to be about 5, prior to adding the mononuclear precursor complex to it and mixing it.

The multinuclear complexes described herein may find particular use in treating a disease, diagnosing a disease or both treating and diagnosing a diseases. The multinuclear complex may therefore be included in a pharmaceutical composition together with a suitable diluent, excipient or carrier.

EXAMPLES

1. Self-Assembly of Dinuclear Complexes

Dinuclear complexes were prepared with Schiff bases and quinoline-based chelators as anchoring ligands.

The Schiff bases are generally of the form $R_cN=CR_aR_b$, $R_c \neq H$) and may include an aromatic hydroxyl-group which is able to bridge two metal complex fragments. The imine moieties of such Schiff base ligands, in turn, coordinate to the respective metal centres and provide flexibility with respect to the nature of $R_c$. $R_c$ may, for example, represent a targeting moiety or a cytotoxic fragment.

a) The Preparation of Dinuclear $^{99}$Tc Complexes

When the Schiff bases, (E)-2-((m-tolylimino)methyl)phenol (hereinafter referred to as Hsal-m-tol), (E)-2-((cyclopentylimino)methyl)phenol (hereinafter referred to as H(5-Me)sal-cpent) and (E)-5-methyl-2-((phenethylimino)methylphenol (hereinafter referred to as H(5-Me)sal-EtPhsal-hex) shown in Scheme 1 below were reacted with fac-[$^{99}$TcCl$_3$(CO)$_3$]$^{2-}$ in acetonitrile at elevated temperature, there was a rapid and substantially quantitative formation of the dinuclear complex [$^{99}$Tc$_2$(μ$_2$-O^N—R$_1$)$_2$(CO)$_6$] (R$_1$=m-toluene 1, =cyclopentane 2, =ethylphenyl 3; R$_2$=H 1, or methyl 2, 3).

The quinoline chelators, 8-hydroxyquinoline, 2-amino-8-hydroxyquinoline, 5,7-dichloro-8-hydroxyquinoline and 8-thioquinoline were used to form Re and Tc dinuclear complexes using the same strategy as with the Schiff bases. Initial experiments with Tc-99 indicate the same behaviour as the Schiff bases.

Scheme 1. (I) Three functionalized Schiff base chelators utilized in the self-assembly study of 1-3. (II) The reaction sequence for either of these Schiff base chelators. In a typical reaction, [NEt$_4$]$_2$[$^{99}$TcCl$_3$(CO)$_3$], the Schiff base ligand and Et$_3$N is dissolved in acetonitrile and heated 80° C. for 3 h. (III) Four functionalised quinoline chelators (Hquin) with H(ox) = 8-hydroxyquinoline, H(2Aox) = 2-amino-8-hydroxyquinoline, H(57Ciox) = 5,7-dichloro-8-hydroxyquinoline and H(ox) = 8-thioquinoline used in the preparation of Tc complexes (1a). (IV) The reaction sequence for either of the quinoline chelators.

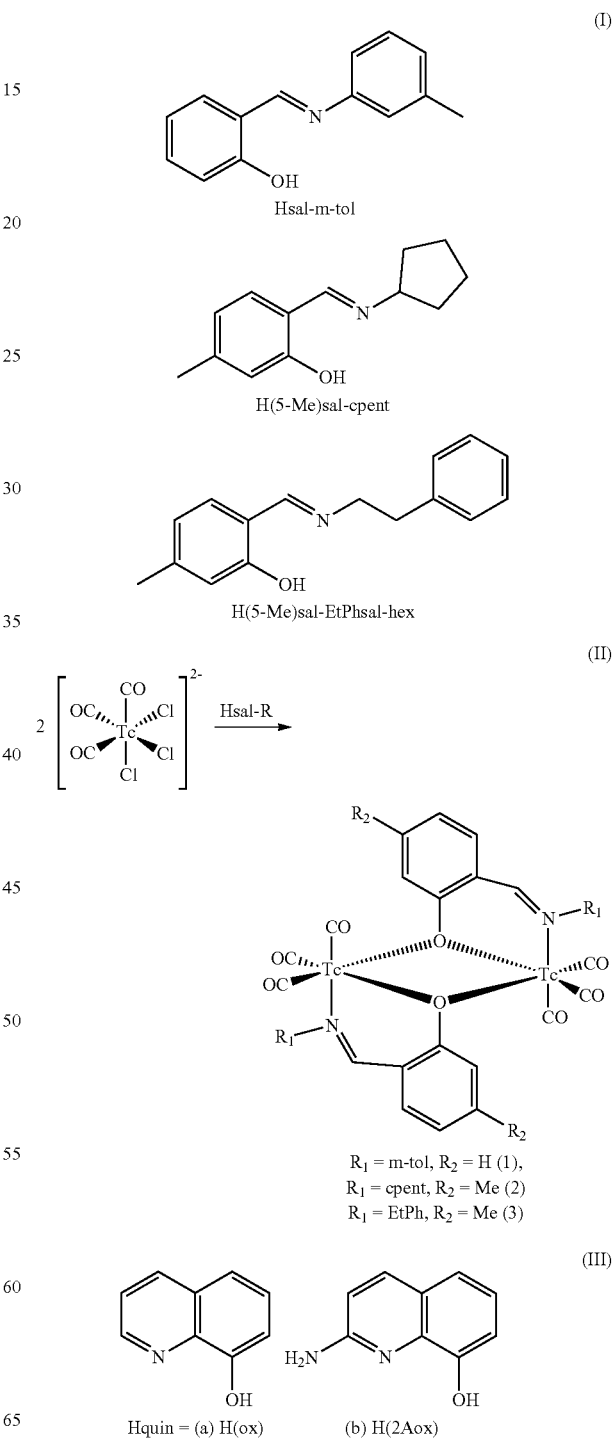

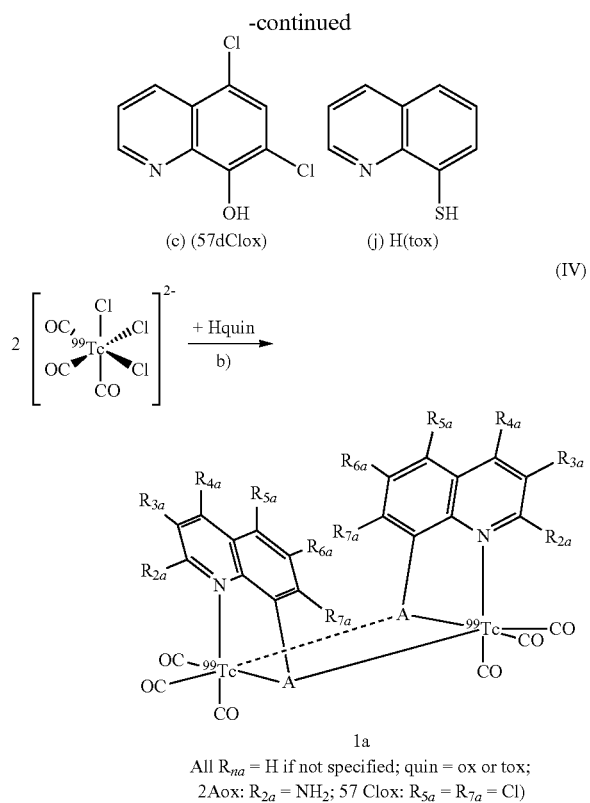

Experimental Section

Synthesis of 1-3 (Indicated for Hsal-m-tol):

$[NEt_4]_2[^{99}Tc(CO)_3Cl_3]$ (25 mg, 0.05 mmol) was dissolved in acetonitrile (3 ml). Hsal-m-tol (16 mg, 0.07 mmol) in acetonitrile (2 ml) was added to the solution. An excess of $Et_3N$ (0.1 ml) was added. After stirring at 80° C. for 3 h, the solution was filtered and the solvent removed under vacuum. The $[Et_4N]Cl$ was removed by extraction with THF. The yellow product 1 was crystallised from a $CH_2Cl_2$ solution (yield: 70%).

Results

Radio-HPLC showed one single peak after the synthesis of compounds 1-3, and minute amounts of side products. The compounds were isolated and characterized by X-ray structure analysis. ORTEP diagrams of complexes 1-3 are shown in FIG. 2.

Important geometric parameters determined from the crystal structures of 1, 2 and 3, respectively are: Bond distances (Å): Tc—C01: 1.899(4), 1.892(4), 1.904(4); Tc—C02 1.922(4), 1.914(4), 1.919(4); TC-C03 1.889(4), 1.899(4), 1.896(4); Tc—O1 2.157(2), 2.158(2), 2.150(2); Tc—N1 2.188(3), 2.172(3), 2.195(3); Tc—O1' 2.189(2), 2.195(2), 2.192(2); Tc—Tc' 2.4210(5), 3.4335(3), 3.4235 (5); O1-O1' 2.6821(3), 2.677(3), 2.671(3). Bond angles (°): OC—Tc—CO: 85.7(1) to 88.1(2) for nine angles; C02-Tc—N1 179.31(13), 176.18(12), 176.13(13); O1-Tc—N1 81.08 (9), 82.01(9), 82.37(10); O1-Tc—O1 76.16(9), 75.87(8), 75.94(9); Tc-O1-Tc' 103.81 (9), 104.12(8), 104.1(1).

All three crystal structures confirm the rigidity of the planar dinuclear frame structure and illustrate the stability induced thereby. There is agreement of the internal geometric parameters such as the Tc—Tc' and O1-O1' bond distances, O1-Tc-01' and O1-Tc-OT angles, and the torsion angle Tc-O1-Tc'—O1' in the planar entity. The crystal structures confirm that the only relative atomic positions that vary are the substituents on the peripheral outer-sphere of the dinuclear compound. This variation is expected to influence the in vivo distribution significantly. Depending on the size of the R groups of the Schiff base chelators, molecular entities in the nanometer range can be prepared in this manner. In respect of complexes 1-3, the dimensions of the dinuclear species when measured from the outer hydrogen atoms of R1-R1' and R2-R2' are 1.7 and 1.3 nm, respectively.

A mononuclear intermediate was not detected during the synthesis of complexes 1-3. However, it must exist at some stage during the course of the reaction. It can thus be concluded that dimerization of such an intermediate occurs rapidly under the reaction conditions and much faster than the initial coordination of one Schiff base to one $[^{99}Tc(CO)_3]^+$ moiety.

The structures of the $[^{99}Tc_2(\mu_2\text{-ox/tox})_2(CO)_6]$ and the $[^{99m}TcRe(\mu_2\text{-ox/tox})_2(CO)_6]$ [ox=hydroxquinolinate; tox=thioquinolinate; Scheme 1, sequence II, (b) and (j), respectively] are modelled on the corresponding rhenium complexes. Preliminary X-ray data confirms that the Tc-99 and the Re complexes are isomorphous (isostructural) which allows structural assumptions as those shown in FIG. 3. Typically, the μO-μO distance in $[^{99}Tc_2(\mu_2\text{-ox})_2(CO)_6]$ is only 2.67 Å compared to the 3.13 Å of the μS-μS distance in $[^{99}Tc_2(\mu_2\text{-tox})_2(CO)_6]$. The corresponding M-M distances are 3.41 and 3.77 Å, respectively. This results in a significant steric distortion in the M-$A_2\mu_2$-M (A=O, S) of 19° in $[^{99}Tc_2(\mu_2\text{-ox})_2(CO)_6]$ compared to only 3° in the $[^{99}Tc_2(\mu_2\text{-tox})_2(CO)_6]$, clearly observable within the structures. This distortion and steric strain is manifested in the relative instability of the ox complexes compared to the tox entities.

The structure in FIG. 3(c) illustrates the coordination in an oligomeric by-product obtained from the $[Re_2(\mu_2\text{-tox})_2(CO)_6]$ synthesis. The trinuclear complex shown in FIG. 3(c) can be obtained in reasonable yields of about 30-40% when the synthesis time is increased. Accordingly, the corresponding $[^{99}Tc_3O_2(\mu\_O)_2(LL)_6]$ and $[^{99m}TcRe_2O_2(\mu\_O)_2(LL)_6]$ trimers are accessible.

b) The Preparation of Dinuclear $^{99}Tc^{99m}Tc$ Complexes

The same reaction used to form the above $^{99}Tc$ dimers was carried out in the presence of fac-$[^{99m}Tc(OH_2)_3(CO)_3]^+$ in acetonitrile.

Experimental Section

Preparation of Dinuclear $^{99m}Tc^{99}Tc$ Complex (Indicated for Hsal-m-Tol):

A solution of fac-$[^{99m}Tc(OH_2)_3(CO)_3]^+$ (0.5 ml) with a typical concentration of $10^{-8}$ mol/dm³ was dried under nitrogen flow, taken up in acetonitrile (1 ml) and added to a solution of $[NEt_4]_2[^{99}Tc(CO)_3Cl_3]$ (40.1 mg, 0.073 mmol) in acetonitrile (3 ml). Hsal-m-tol (17 mg, 0.080 mmol) in acetonitrile (2 ml) and an excess of $NEt_3$ (0.1 ml drops) were added and the solution was stirred at 80° C. for 3 h.

Results

The complex that includes $^{99m}Tc$ was observed with a γ-trace and had a retention time that is equal to the retention time of the complex that only includes $^{99}Tc$, observed with a β-trace. To unambiguously determine the identity of the $^{99}Tc_2$ and the $^{99}Tc^{99m}Tc$ compounds, they were co-injected into HPLC and the retention times compared as shown in FIG. 4. The equal retention times confirmed the formation of $[^{99}Tc^{99m}Tc \ (\mu_2\text{-O}^\frown N-R_1)_2(CO)_6]$.

c) The Preparation of Dinuclear $^{99m}Tc$—Re Complexes

Homologous complexes to the dinuclear complexes 1-3, but including one $^{99m}Tc$ metal centre and one Re metal centre together with a large amount of $Re_2$ homologues were prepared.

It was found that the dimerization reaction of fac-[$^{99}$TcCl$_3$(CO)$_3$]$^{2-}$ does not take place with fac-[ReBr$_3$(CO)$_3$]$^{2-}$ in the presence of the Schiff bases of Scheme 1 when carried out in an organic solvent or a water/MeOH mixture. The reaction in the presence of the Schiff ligand Hsal-m-tol yielded exclusively mononuclear complexes of the type fac-[Re(O^N-m-tol)(CO)$_3$(Sol)] (4) as per reaction a) in Scheme 2 below.

Scheme 2. Self-assembly of a dinuclear $^{99m}$TcRe complex. Reaction a) rhenium only yields mononuclear complexes (4). Reaction b) $^{99m}$Tc only yields dinuclear complexes (1-3) and reaction c) mixture of $^{99m}$Tc and Re gives mononuclear rhenium complexes (4) and mixed $^{99m}$TcRe complexes (5). Reaction conditions for c): [NEt$_4$]$_2$[ReBr$_3$(CO)$_3$] and fac-[$^{99m}$Tc(OH$_2$)$_3$(CO)$_3$]$^+$ where dissolved in acetonitrile. Hsal-m-tol and NEt$_3$ were added and the mixture was heated to 80° C. for 3 h.

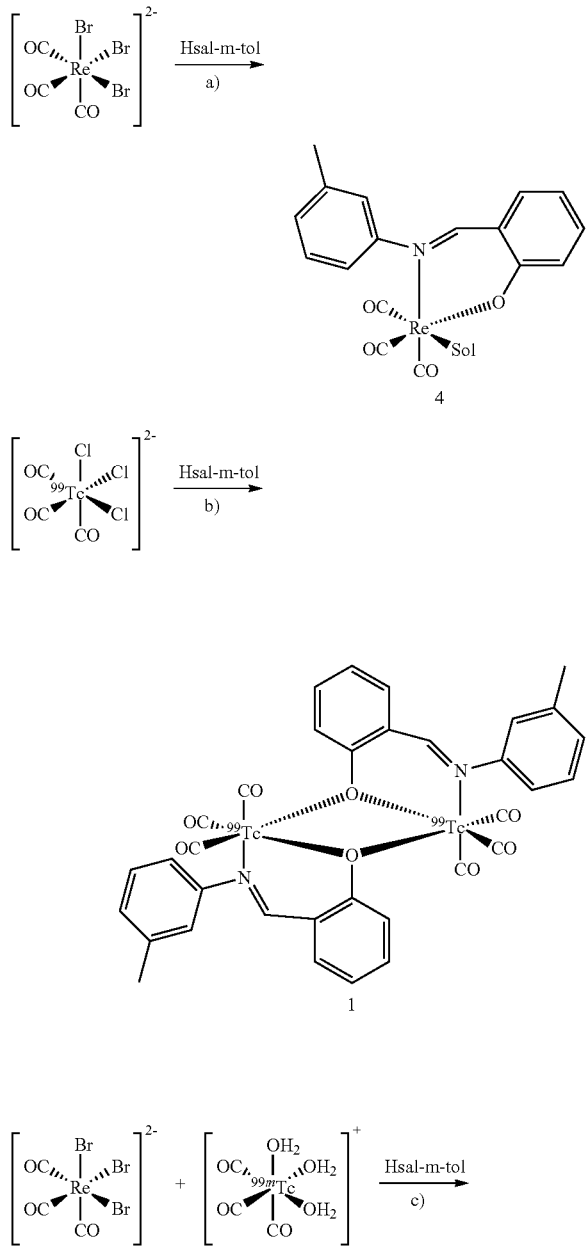

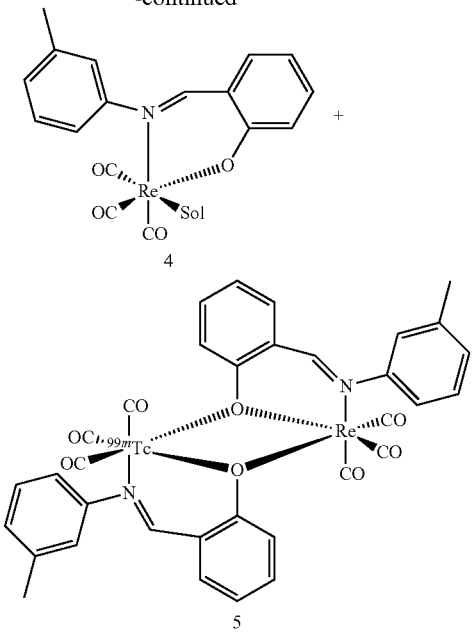

The different behaviour of the Re and Tc homologues is believed to be due to substantially different reaction kinetics in low oxidations states rather than being due to thermodynamic features.

It was also tested how a mixture of fac-[ReBr$_3$(CO)$_3$]$^{2-}$ and fac-[$^{99m}$Tc(OH$_2$)$_3$(CO)$_3$]$^+$ would behave in acetonitrile in analogy to the $^{99}$Tc reaction described above, and in the presence of the Schiff bases. Reaction c) in Scheme 2 was carried out under the same conditions as reaction a).

Experimental Section

Preparation of Dinuclear $^{99m}$TcRe Complex (5):

A solution of fac-[$^{99m}$Tc(OH$_2$)$_3$(CO)$_3$]$^+$ (0.5 ml) with a typical concentration of 10$^{-8}$ mol/dm$^3$ was dried under nitrogen flow, taken up in acetonitrile (1 ml) and added to a solution of [NEt$_4$]$_2$[ReBr$_3$(CO)$_3$] (20 mg, 0.026 mmol) in acetonitrile (1 ml). Hsal-m-tol (6 mg, 0.028 mmol) in acetonitrile (1 ml) and an excess of NEt$_3$ (8 drops) were added and the solution was stirred at 80° C. for 3 h.

Results

The reaction with Hsal-m-tol gave the mononuclear rhenium complex (4) in quantitative yields as well as the mixed-metal dinuclear complex [$^{99m}$TcRe(μ$_2$-O^N-m-tol)$_2$(CO)$_6$] (5). Since the $^{99m}$Tc precursor complex is present at very low concentration in the nanomolar range, dimerization to yield the $^{99m}$Tc analogue of 1 is not expected for kinetic reasons. If the mononuclear Re complex 4 is the most stable form, dimerization with the $^{99m}$Tc fragment and an additional ligand is also not expected. Accordingly, the dinuclear complex 5 is thermodynamically favored over the monomer 4 which allows for the formation of a mixed-element dinuclear complex. HPLC traces of the crude reaction mixtures are shown in FIG. 4.

Dinuclear complexes similar to [$^{99m}$TcRe(μ$_2$-O^N-m-tol)$_2$(CO)$_6$] (5) but where the Schiff base chelator is H(5-Me)sal-cpent or H(5-Me)sal-EtPhsal-hex as per Scheme 1 above were also prepared with similar results that were described above with reference to the chelator, Hsal-m-tol, obtained.

Similar synthetic procedures for the corresponding quinoline-based dinuclear complexes were observed and are further envisaged as per Scheme 3.

Scheme 3. Strategy for self-assembly of the dinuclear $^{99m}$TcRe complex with quinoline chelators. Reaction a) yields mononuclear complexes (4a) but with heating for 3-5 hours the dinuclear Re$_2$ dimer (4b) is obtained. Synthetic protocols similar to those described above in Scheme 2 for the Schiff base systems are illustrated and envisaged to obtain the dinuclear species 1a and 5a. Upon prolonged heating the trimeric complex of the general formula VII of Figure 3(c) is obtained in reasonable yield.

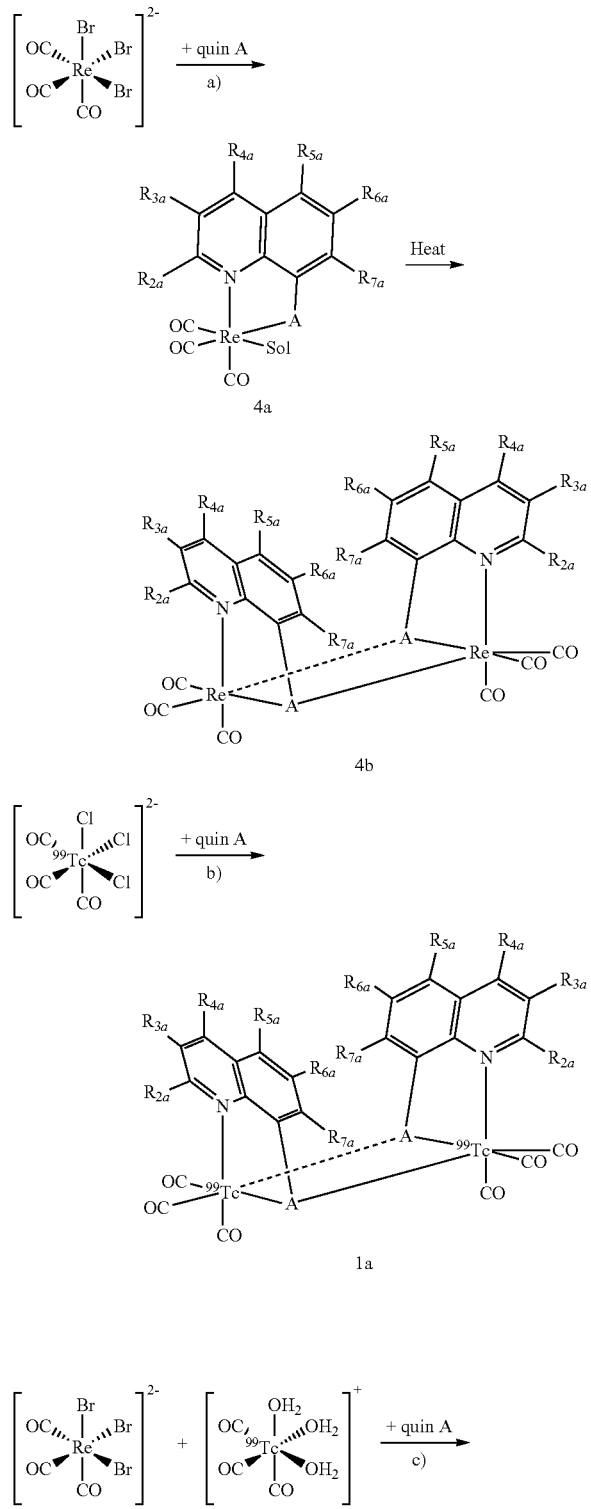

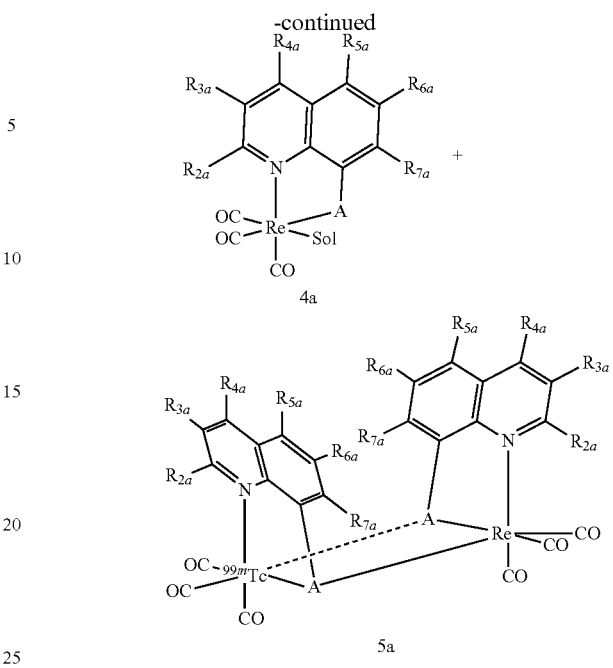

The self-assembly process in the presence of bidentate bridging chelators leads to the formation of a well-defined $^{99m}$Tc—Re complexes. The combination of the two elements, $^{99m}$Tc and Re in one and the same compound may open up a new avenue of study in theranostics. The dinuclear complexes that include $^{99m}$Tc can be traced so as to potentially follow their in vivo pharmacology. It is foreseen that the Schiff base framework can be of any kind or structure and that it may also include a targeting molecule or a cytotoxic agent.

Dinuclear complexes, labelled with $^{99m}$Tc can be prepared in a single step. In contrast to the classic labelling procedure with bifunctional ligands and a single $^{99m}$Tc atom, the metals self-assemble into a dinuclear cluster as the transition metal precursor complexes act as "ligands".

The compounds described in this example include variable moieties, namely $R_1$ and $R_2$ in the Schiff base ligands and $R_{2a}$-$R_{7a}$ in the quinoline-based ligands, which may be selected or functionalised to be bioactive or diagnostic in nature. Furthermore, the metal centres may exert therapeutic or diagnostic functions.

A dinuclear complex incorporating $^{99m}$Tc is unlikely to form in the exclusive presence of mononuclear $^{99m}$Tc complexes since its concentration is in the nanomolar range. Very small concentrations of these isotopes can be generated at a time from $^{99}$Mo and second order reaction kinetics are therefore slow. The preparation of the above dinuclear complexes that include $^{99m}$Tc provides a unique approach in which homologous metal complexes are used as building blocks to prepare radiopharmaceuticals. Moreover, it may offer a convenient and uncomplicated way of obtaining pre-designed nanomaterial molecular entities, which can be varied for functionality and size.

2. Self-Assembly of Tetranuclear Complexes

Model reactions for both of the conceptual pathways A and B of FIG. 1 were carried out with mononuclear Re complexes as precursor transition metal complexes to further demonstrate the feasibility of preparing multinuclear complexes labelled with $^{99m}$Tc.

a) The Preparation of Tetranuclear $^{99m}$Tc—Re Complexes Via a Trinuclear Precursor Complex (Pathway A)

The introduction of a complex fragment into an incomplete multinuclear cluster according to pathway A requires a sequential build-up of precursors into a final product. For example, a stepwise buildup of the tetranuclear complex [Re$_4$($\mu_3$-OH)$_4$(CO)$_{12}$] with cubane-like structure was carried out. The incomplete, anionic trinuclear complex forms stepwise from the precursor fac-[Re(OH$_2$)$_3$(CO)$_3$]$^+$ (6) via [Re$_2$($\mu_2$-OH)$_3$(CO)$_6$]$^-$ (7) and [Re$_3$($\mu_2$-OH)$_3$($\mu_3$-OH)(CO)$_9$]$^-$ (8) under mildly basic conditions as shown in Scheme 4 below. $^{99}$Tc homologues of 6, 7 and 8 were also prepared. Similar multinuclear complexes were also prepared with alcoholato or thiolato bridges.

Scheme 4. Stepwise build-up of the trinuclear cluster [Re$_3$($\mu_2$-OH)$_3$($\mu_3$-OH(CO)$_9$]$^-$ (8). The pre-assembly leaves a vertex for coordination to $^{99m}$Tc. "Re" denominates the fac-[Re(CO)$_3$]$^+$ fragment as indicated in 8.

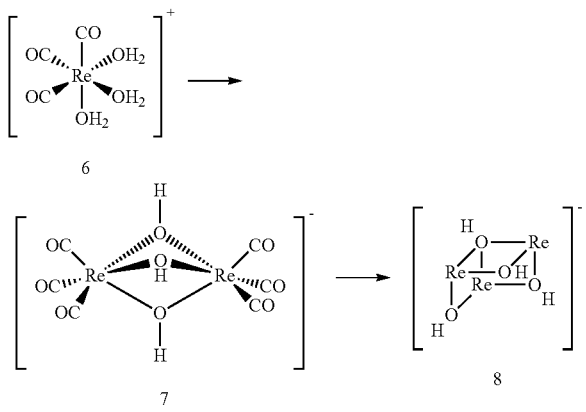

The metals are bridged by a single atom, potentially bound to further organic functions, coordinating or just pendent. For the fac-[Re(CO)$_3$]$^+$ fragment, this might be an oxygen from an alcoholato group (alkoxy ligand) or a sulfur from a thiolate, i.e. from $\mu^2$- or $\mu^3$-O/SR motives. Oxygen, sulfur or selenium may be the coordinating atoms as they coordinate weakly as terminal donors and exhibit a tendency to bridge to further metal-centers to form multinuclear clusters with a single atom bridge. Incomplete clusters such as [Re$_3$($\mu_2$-OH)$_3$($\mu_3$-OH)(CO)$_9$]$^-$ (8) are therefore prone to coordinate to further metal centers or complex fragments and may therefore be labelled with $^{99m}$Tc.

The reaction of the incomplete, separately prepared Re$_3$ cluster 8 with the $^{99m}$Tc precursor fac-[$^{99m}$Tc(OH$_2$)$_3$(CO)$_3$]$^+$ according to pre-assembly approach of pathway A in Scheme 1 leads to a cube-like cluster incorporating $^{99m}$Tc. The missing vertex of the Re$_3$ cluster is filled with the fac-[$^{99m}$Tc(CO)$_3$]$^+$ fragment or another metal to complete the cube. Completing the cube with the fac-[Re(CO)$_3$]$^+$ moiety yields the extremely stable cubane complex [Re$_4$($\mu_3$-OH)$_4$(CO)$_{12}$].

Experimental Section
Preparation of Tetranuclear $^{99m}$TcRe$_3$ Cluster 9 from 8 (Pathway A):
The pH of an aqueous fac-[$^{99m}$Tc(OH$_2$)$_3$(CO)$_3$]$^+$-solution (0.9 ml) with a typical concentration of 10$^{-8}$ mol/dm$^3$ was adjusted to 5 with HCl and an acetate buffer (0.2M, 0.2 ml). This-solution (0.5 ml) was transferred to a N$_2$-purged microwave vial containing 8 (3.0 mg, 2.97 µmol) and heated in a microwave for 10 min at 100° C. HPLC analysis evidences 94% yield of 9. HPLC: 21.2 min.

Results
When the trinuclear complex, [Re$_3$($\mu_2$-OH)$_3$($\mu_3$-OH)(CO)$_9$]$^+$ (8), is reacted with fac-[$^{99m}$Tc(OH$_2$)$_3$(CO)$_3$]$^+$, the mixed metal tetranuclear cluster [$^{99m}$TcRe$_3$($\mu_3$-OH)$_4$(CO)$_{12}$] (9) formed in quantitative yields. HPLC coinjection of the homologues [$^{99m}$TcRe$_3$($\mu_3$-OH)$_4$(CO)$_{12}$] (9) and [Re$_4$($\mu_3$-OH)$_4$(CO)$_{12}$] (10) and comparing the UV/vis and gamma-trace retention times confirmed the identity of the two compounds and these HPLC traces of 9 and 10 are shown in FIG. 6.

Since the rhenium cluster 8 is present in large excess relative to the $^{99m}$Tc complex, which is typically present in the nanomolar concentration range, and further in light of the six hour half-life of $^{99m}$Tc the majority of the product is the tetranuclear Re-complex following the labelling reaction.

b) The Preparation of Tetranuclear $^{99m}$Tc—Re Complexes by Self-Assembly of Mononuclear Precursor Complexes (Pathway B)

A self-assembly strategy involving a one-step, one-pot reaction to form the tetranuclear $^{99m}$TcRe-complex 9 from a slightly acidic mixture of 6 and fac-[$^{99m}$Tc(OH$_2$)$_3$(CO)$_3$]$^+$ was carried out and the reaction is shown in Scheme 5 below.

Scheme 5. Self-assembly reaction between the mono-nuclear precursors 6 and its $^{99m}$Tc homologue under mildly acidic conditions yields the tetra-nuclear cubane type clusters 9 and 10. "Re" in 9 and 10 represents the fac-[Re(CO)$_3$]$^+$ fragments (CO ligands not shown for clarity).

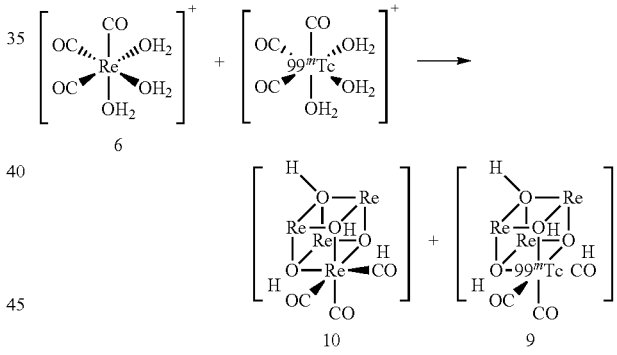

Experimental Section
Preparation of Tetranuclear $^{99m}$TcRe$_3$ Cluster 9 from 6 (Scheme 4, Pathway B):
The pH of an aqueous solution of fac-[$^{99m}$Tc(OH$_2$)$_3$(CO)$_3$]$^+$ (0.5 ml) with a typical concentration of 10$^{\text{-}8}$ mol/dm$^3$ was adjusted to 5 as described before and transferred to a N$_2$-purged microwave vial containing [NEt$_4$]$_2$[ReBr$_3$(CO)$_3$] (3.1 mg, 4.02 µmol). Stirring at 20° C. for 10 min and subsequent heating at 100° C. in a microwave oven for 10 min afforded 9 in 90% yield according to HPLC analysis.

Results
The one-step reaction shown in Scheme 4 gave quantitative yields of 9 beside large amounts of 10 due to the excess of 6 used in the reaction. An HPLC trace of the crude reaction mixture without coinjection with 10 is shown in FIG. 7. It shows the UV-trace of 10 and the γ-trace of the tetranuclear $^{99m}$TcRe-complex (9).

The self-assembly strategies demonstrate how homologous precursor metal complexes of different elements, but incorporating metals of the same group in the periodic table having similar chemical and physical properties, can be used as building blocks for forming versatile multinuclear and heteronuclear complexes. Multinuclear complexes that include a medical radioisotope that is only available in small concentrations can be prepared. This approach which allows for the incorporation of a radioisotope in a multinuclear complex despite the presence of extremely small concentrations of the radioisotope and may find wide application. Its use may extend beyond the field of medical theranostics, to any other potential application where multinuclear complexes including a particular radioisotope are required, but where the radioisotope is a scarce resource or is only available in small amounts for other reasons.

In terms of their application in life sciences, multinuclear complexes may potentially deliver more than one targeting or bioactive moiety. For example, more than one therapeutic metal centre or other therapeutic moiety can be can be delivered at a specific time from the coordination periphery of the complex to the biological target, once it is bound to a corresponding biological target receptor. The difficulties of preparing a well-defined composition and the integration of a targeting/bioactive entity may be at least partially alleviated by the above described methods of preparing multinuclear complexes by self-assembly.

The multinuclear complexes that include a radioisotope or radioelement that can be detected by medical equipment may find use in theranostics. For example, if one metal in a multinuclear cluster is a γ-emitter, the complex as a whole has theranostic potential. The radioisotope or radioelement provides a non-invasive method for following the biological behavior of the multinuclear complexes. Homologous precursor complexes may be selected such that the multinuclear metal complex that forms by self-assembly includes multiple targeting and/or cytotoxic agents on a single complex. This potentially increases their versatility with respect to their mode of action in biological target finding and/or drug delivery.

Conveniently, the multinuclear complexes or clusters can be prepared along self-assembly pathways, either form mononuclear precursors or by completing a pre-assembled cluster fragment, i.e. a fragment which serves as a ligand. For example, an incomplete and separately prepared $M_3$ (M=Mn, Re or Tc) cluster can incorporate a fac-$[^{99m}Tc(CO)_3]^+$ moiety to complete a cube. The bridging ligands of the example were hydroxides, but a person skilled in the art would appreciate that these may be replaced with thiols, functionalized alkoxides, functionalized thiolates and functionalized selenolates amongst others. A one pot reaction with the mononuclear precursors leads in one step to the product. Secondly with bidentate bridging ligands, such as Schiff bases or quinoline-based chelators, dinuclear complexes can be prepared in a single step. The bidentate bridging ligands may be further functionalised for a selected application of such multinuclear complexes. The multinuclear complexes and processes to prepare them described herein provide more versatile complexes as scaffolds for further derivatisation that may incorporate different modalities beyond that which is possible for mononuclear complexes.

Throughout the specification unless the content requires otherwise the word 'comprise' or variations such as 'comprises' or 'comprising' will be understood to imply the inclusion of a stated integer or group of integers but not the exclusion of any other integer or group of integers.

The invention claimed is:

1. A multinuclear complex comprising:
   a transition metal selected from the group consisting of manganese (Mn), technetium (Tc), rhenium (Re), and any isotope thereof;
   a technetium-99m ($^{99m}Tc$) radioisotope
   a bridging ligand coordinated to the transition metal and the $^{99m}Tc$ radioisotope to link the transition metal and the $^{99m}Tc$ radioisotope by a single coordinating atom; and
   pendent ligands coordinated to each of the transition metal and the $^{99m}Tc$ radioisotope.

2. The multinuclear complex as claimed in claim 1, wherein when the transition metal is rhenium, it is a β-radiation emitting isotope of rhenium selected from rhenium-186 ($^{186}Re$) or rhenium-188 ($^{188}Re$), and when the transition metal is technetium it is the technetium-99 ($^{99}Tc$) isotope.

3. The multinuclear complex as claimed in claim 1, having the general formula [$^{99m}TcM(\mu_2-L)_2(CO)_6$], wherein
   M is Mn, Re, Tc or any isotope thereof, and
   $\mu_2$-L is a bidentate bridging ligand having at least two coordinating atoms independently selected from the group consisting of an oxygen atom, a sulphur atom, a selenium atom, a nitrogen atom, a carbon atom and a phosphorus atom, wherein one of the coordinating atoms of the bidentate ligand coordinates to both $^{99m}Tc$ and M as a bridging coordinating atom and the other coordinating atom of the same bidentate ligand coordinates to one of $^{99m}Tc$ or M.

4. The multinuclear complex as claimed in claim 3, wherein the bidentate ligand ($\mu_2$-L) is a Schiff base chelator.

5. The multinuclear complex as claimed in claim 4, having the general formula (I):

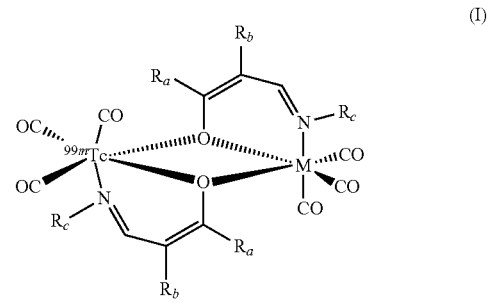

(I)

wherein
   M is Mn, Re, Tc or any isotope thereof,
   $R_a$, $R_b$ and $R_c$ are each independently a hydrogen, an optionally substituted C1-C10 linear or branched alkyl, an optionally substituted aryl, an optionally substituted heteroaryl, an optionally substituted C5-C10 carbocyclyl or an optionally substituted heterocyclyl group and wherein $R_a$, $R_b$ and $R_c$ each include one or more heteroatoms selected from the group consisting of an oxygen, nitrogen, sulphur, selenium, or halogen atom,
or $R_a$ and $R_b$ together is an optionally substituted cyclic aromatic hydrocarbon, an optionally substituted aromatic heterocycle, an optionally substituted polycyclic aromatic hydrocarbon selected from the group consisting of naphthalene, biphenyl, anthracene, and phenanthrene, an optionally substituted cyclic hydrocarbon or an optionally substituted heterocycle.

6. The multinuclear complex as claimed in claim 5, wherein the halogen is selected from the group consisting of fluorine, chlorine, bromine and iodine.

7. The multinuclear complex as claimed in claim 5, wherein a pendent functional group on the aromatic structure of the polycyclic aromatic hydrocarbon selected from the group consisting of naphthalene, biphenyl, anthracene, and phenanthrene includes one or more hetero atoms selected from the group consisting of oxygen, nitrogen, sulphur, selenium, and phosphorus.

8. The multinuclear complex as claimed in claim 3, wherein the bidentate ligand ($\mu_2$-L) is a quinoline-based chelator.

9. The multinuclear complex as claimed in claim 8 having the general formula (IV)

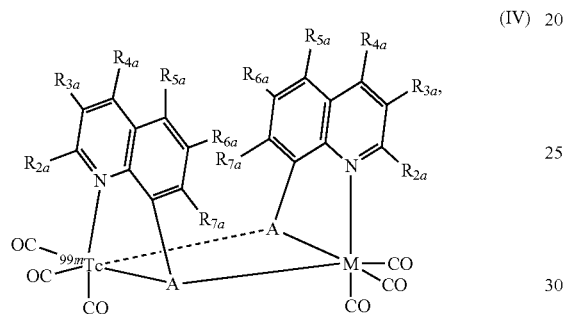

(IV)

wherein

M is Mn, Re, Tc or any isotope thereof;

A is oxygen, sulfur or selenium; and $R_{2a}$ to $R_{7a}$ are each independently a hydrogen, halogen, nitro, nitrile, amine, carboxylate, aldehyde, an optionally substituted C1-C10 linear or branched alkyl, an optionally substituted aryl, an optionally substituted heteroarylan optionally substituted C5-C10 carbocyclyl or an optionally substituted heterocyclyl group and wherein $R_{2a}$ to $R_{7a}$ each include one or more heteroatoms selected from the group consisting of an oxygen, nitrogen, sulphur, selenium, or halogen atom, or $R_{2a}$ to $R_{7a}$ together is an optionally substituted polycyclic aromatic hydrocarbon selected from the group consisting of naphthalene, biphenyl, anthracene, and phenanthrene.

10. The multinuclear complex as claimed in claim 1 having the general formula (III):

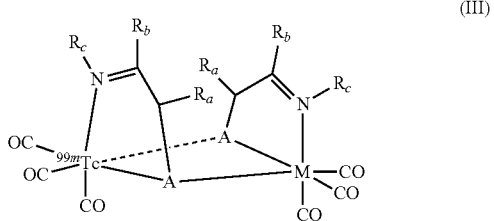

(III)

wherein

M is Mn, Re, Tc or any isotope thereof,

A is oxygen, sulfur or selenium;

$R_a$, $R_b$ and $R_c$ are each independently a hydrogen, an optionally substituted C1-C10 linear or branched alkyl, an optionally substituted aryl, an optionally substituted heteroaryl, an optionally substituted C5-C10 carbocyclyl or an optionally substituted heterocyclyl group and wherein $R_a$, $R_b$ and $R_c$ each include one or more heteroatoms selected from the group consisting of an oxygen, nitrogen, sulphur, selenium, or halogen atom, or $R_a$ and $R_b$ together is an optionally substituted cyclic aromatic hydrocarbon, an optionally substituted aromatic heterocycle, an optionally substituted polycyclic aromatic hydrocarbon selected from the group consisting of naphthalene, biphenyl, anthracene and phenanthrene, an optionally substituted cyclic hydrocarbon or an optionally substituted heterocycle.

11. The multinuclear complex as claimed in claim 1 having the general formula (II):

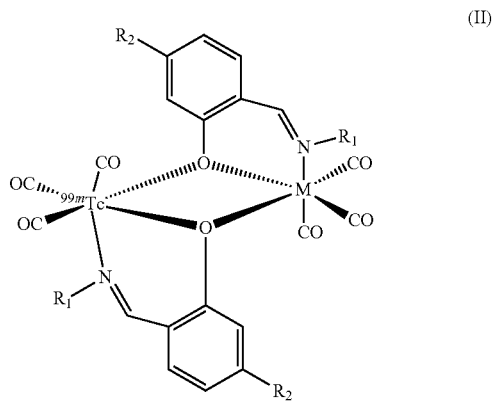

(II)

wherein M is Mn, Re, Tc or any isotope thereof, $R_1$ is an m-toluene group, a cyclopentane group, or an ethylbenzene group and $R_2$ is hydrogen or a methyl group.

12. The multinuclear complex as claimed in claim 1 having the general formula [$^{99m}$TcM$_2$O$_2$($\mu$-L)$_2$(LL)$_6$], wherein M is Mn, Re, Tc or any isotope thereof;

$\mu$-L is a bridging ligand selected from oxides ($O^{2-}$) or sulphides ($S^{2-}$); and LL is a bidentate pendent ligand separately coordinated to each of $^{99m}$Tc and M and having at least two coordinating atoms independently selected from the group consisting of an oxygen atom, a sulphur atom, a selenium atom, a nitrogen atom, a carbon atom and a phosphorus atom.

13. The multinuclear complex as claimed in claim 12 having the general formula (V):

(V)

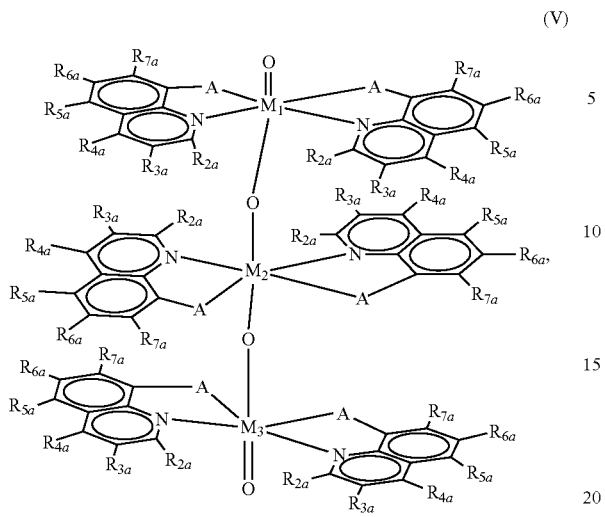

wherein at least one of $M_1$, $M_2$ or $M_3$ is $^{99m}$Tc and the remaining metal centres of $M_1$, $M_2$ or $M_3$ are Mn, Re, Tc or any isotope thereof and in any combination thereof;

A is an oxygen, sulfur or selenium atom; and $R_{2a}$ to $R_{7a}$ are each independently a hydrogen, halogen, nitro, nitrile, amine, carboxylate, aldehyde, an optionally substituted C1-C10 linear or branched alkyl, an optionally substituted aryl, an optionally substituted heteroaryl an optionally substituted C5-C10 carbocyclyl or an optionally substituted heterocyclyl group and wherein $R_{2a}$ to $R_{7a}$ each optionally include one or more heteroatoms selected from the group consisting of an oxygen, nitrogen, sulphur, selenium, or halogen atom, or $R_{2a}$ to $R_{7a}$ together is an optionally substituted polycyclic aromatic hydrocarbon selected from the group consisting of naphthalene, biphenyl, anthracene and phenanthrene.

14. The multinuclear complex as claimed in claim 1, having the general formula: $[^{99m}TcM_3(L)_4(CO)_{12}]$, wherein M is Mn, Re, Tc, or any isotope thereof and L is a bridging ligand having a coordinating atom selected from the group consisting of an oxygen atom, a sulfur atom, and a selenium atom.

15. The multinuclear complex as claimed in claim 14, having a cubane structure and the general formula (VI):

(VI)

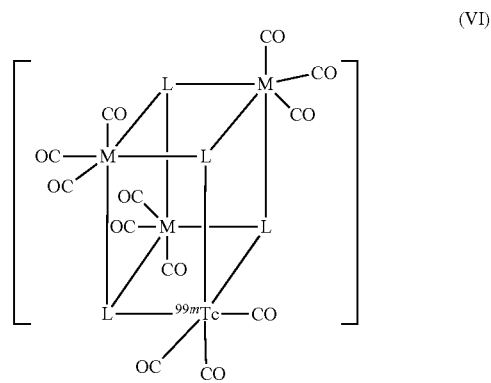

wherein M is Mn, Re, Tc or any isotope thereof and L is a monodentate bridging ligand having a coordinating atom selected from the group consisting of an oxygen atom, a sulfur atom, and a selenium atom.

16. The multinuclear complex as claimed in claim 15, having the molecular formula $[^{99m}TcRe_3(\mu_3\text{-}OH)_4(CO)_{12}]$ and the structural formula (VII):

(VII)

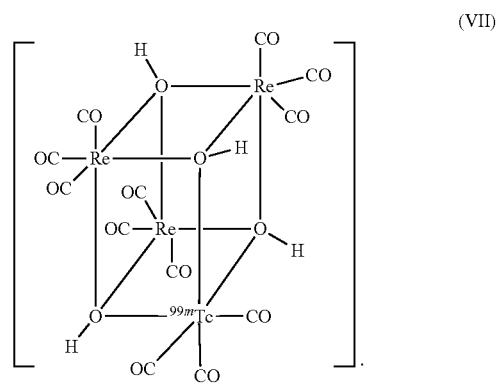

17. The multinuclear complex as claimed in claim 15, wherein the bridging ligands (L) are selected from the group consisting of hydroxides (OH), thiols (SH), optionally functionalised C1-C10 alkoxides, optionally functionalised C1-C10 thiolates and optionally functionalised C1-C10 selenolates.

18. A pharmaceutical composition comprising a multinuclear complex as claimed in claim 1 and a diluent, excipient or carrier.

* * * * *